(12) United States Patent
Ho et al.

(10) Patent No.: US 7,665,842 B2
(45) Date of Patent: *Feb. 23, 2010

(54) METHOD AND APPARATUS FOR CONTROLLING PERIPHERAL IMAGE POSITION FOR REDUCING PROGRESSION OF MYOPIA

(75) Inventors: Arthur Ho, Coogee (AU); Earl Leo Smith, III, Houston, TX (US); Padmaja Sankaridurg, Marboubra (AU); Brien Anthony Holden, Kingsford (AU)

(73) Assignee: Institute for Eye Research, Sydney, New South Wales (AU)

( * ) Notice: Subject to any disclaimer, the term of this patent is extended or adjusted under 35 U.S.C. 154(b) by 387 days.

This patent is subject to a terminal disclaimer.

(21) Appl. No.: 11/622,246

(22) Filed: Jan. 11, 2007

(65) Prior Publication Data

US 2007/0159601 A1 Jul. 12, 2007

Related U.S. Application Data

(60) Provisional application No. 60/758,316, filed on Jan. 12, 2006, provisional application No. 60/782,658, filed on Mar. 15, 2006.

(51) Int. Cl.
*G02C 7/02* (2006.01)
*A61B 3/10* (2006.01)

(52) U.S. Cl. .................. 351/177; 351/205; 351/221

(58) Field of Classification Search ............... 351/177, 351/205, 221

See application file for complete search history.

(56) References Cited

U.S. PATENT DOCUMENTS

| | | | |
|---|---|---|---|
| 6,045,578 A | 4/2000 | Collins et al. | |
| 6,343,861 B1 | 2/2002 | Kris et al. | |
| 6,752,499 B2 | 6/2004 | Aller | |
| 7,025,460 B2* | 4/2006 | Smitth et al. | 351/221 |
| 7,401,922 B2* | 7/2008 | Legerton | 351/246 |
| 7,503,655 B2* | 3/2009 | Smith et al. | 351/246 |
| 2003/0058404 A1 | 3/2003 | Thorn et al. | |
| 2004/0237971 A1 | 12/2004 | Radhakrishnan et al. | |
| 2006/0082729 A1 | 4/2006 | To et al. | |

FOREIGN PATENT DOCUMENTS

| | | |
|---|---|---|
| WO | 2005/055891 | 6/2005 |
| WO | 2006/004440 | 1/2006 |

* cited by examiner

*Primary Examiner*—Scott J Sugarman
(74) *Attorney, Agent, or Firm*—Smith Moore Leatherwood LLP

(57) ABSTRACT

A method and apparatus are disclosed for controlling optical aberrations to alter relative curvature of field by providing optical devices and methods comprising the repositioning of peripheral off-axis focal points relative to the retina to produce stimulus for influencing the progression of refractive error while simultaneously controlling the position of the central focal point near to the retina to provide clear central vision and simultaneously providing zones of controlled peripheral defocus and other optical aberrations to improve peripheral vision for select directions of gaze.

22 Claims, 14 Drawing Sheets

METHOD AND APPARATUS FOR CONTROLLING PERIPHERAL IMAGE POSITION FOR REDUCING PROGRESSION OF MYOPIA

CROSS-REFERENCE

This application claims benefit of priority from co-pending and commonly assigned U.S. Provisional Patent Application Nos. 60/758,316 filed Jan. 12, 2006 and 60/782,658 filed Mar. 15, 2006.

FIELD OF THE INVENTION

The present application is directed generally to methods and systems for the treatment of progression of refractive error. It represents a novel and unobvious advance over commonly assigned U.S. Pat. No. 7,025,460.

In particular, the present invention is directed to methods, systems and apparatuses for retarding or eliminating the progression of myopia in an individual by controlling off-axis aberrations, thereby manipulating the relative curvature of field of a visual image while simultaneously providing clear imaging at select non-central directions and points of vision.

Myopia, also known as shortsightedness or nearsightedness, is a type of refractive error of the eye. Refractive error, an optical state of the eye in which the focus of the eye is incorrect causing blurred vision, includes myopia, hyperopia (farsightedness or longsightedness) and refractive astigmatism. In myopia, the visual focus defect is such that distant objects (items in the scenery being viewed by the eye) appear blurred because their images are focused in front of the retina instead of on the retina. Myopia is a common visual disorder, affecting around a quarter of the adult population of the USA, and its prevalence is increasing. In some countries, most notably in the Asian region, the prevalence of myopia is now higher than 80% in school-age children in some countries. Thus, a large percentage of the world's population has myopia at a level that requires some form of optical correction in order to see clearly. It is also known that myopia progresses—regardless of age of onset, myopia tends to increase in amount requiring stronger and stronger correction. High amounts of myopia can lead to some forms of retinal pathology; with increased risk of retinal detachment, posterior cataract and glaucoma. In addition, accompanying this visual disorder are personal, social and financial burdens to the individual and to the community. These include the direct costs of vision correction and management (which amounts to several billion dollars a year), as well as indirect costs such as productivity and quality of life. The visual and potential pathological effects of myopia and its consequent inconvenience and cost to the individual and community makes it desirable to have effective strategies to prevent or delay the onset of myopia, to stop or slow the progress, or limit the amount of myopia occurring in both children and young adults.

Currently, the blurred vision of individuals with refractive errors including those with myopia is commonly improved by the prescribing of optical corrections. These optical corrections are delivered using a wide range of vision correction devices including spectacles, contact lenses and refractive surgery. These corrections optically change the position of the focus of the visual image so it is lying on the retina, thereby restoring clear vision. However, these do little if anything to slow or stop the progression of myopia and, according to at least some research findings, may actually promote the progression of myopia.

Strategies to prevent or slow myopia have been suggested that involve pharmacological interventions such as atropine or pirenzipine. However, the potential disadvantages associated with the long-term use of such pharmacological substances may render such modalities unattractive. Other strategies include the use of vision training. Such modalities, which in practice, can only be delivered sporadically and requires rigorous attentiveness on the part of the patient, may have questionable value due to potential incorrect usage or poor compliance by the patient.

Since the individual with refractive error would typically already be wearing a vision correction device and typically for long durations, a method for reducing or eliminating the progression of myopia that is optically-based and that may be incorporated in a vision correction device would be extremely attractive due to the ensured compliance by the individual as well as the long duration of treatment that can be achieved.

BACKGROUND TO THE INVENTION

A number of optical methods have been developed over the years to attempt to reduce or eliminate the progression of myopia. These methods attempt to extend their associated vision correction device to one which is a vision (i.e. refractive error) treatment device. In this document, "vision correction devices" that employ optical methods for eliminating or reducing the progression of refractive errors will be called "vision treatment devices".

One much-attempted optical method is "under-correction" in which the wearer is prescribed an optical power less than necessary to fully correct his refractive error. Since the position of the visual image is not relocated to the retina, constant blurred vision is an implicit and undesirable consequence of the under-correction method. Due to the constant blurred vision, compliance of the wearer to maintain this method of treatment is likely to be poor.

Other optical methods employ bifocal or progressive aspheric lens spectacles or bifocal contact lenses as potential strategies for retarding the progression of myopia. For example, U.S. Pat. No. 6,343,861 to Kris discloses the use of a progressive ophthalmic lens designed to reduce the rate of juvenile myopia progression. U.S. Pat. No. 6,752,499 to Aller discloses a method for treating myopia progression in patients who also exhibit near point esophoria by selectively prescribing bifocal contact lenses. WO 2006/004440 to Phillips discloses the use of bifocal contact lenses with various arrangements of vision correction area and myopic defocus area to counter progression of myopia. US 2006/0082729 to describes the use of Fresnel-type lenses to produce two refractive powers (i.e. a bifocal effect) to treat the progression of myopia.

However, studies on the efficacy of methods that employ bifocal devices generally show only limited efficacy. In the case of bifocal or progressive spectacles, compliance of the wearer to always look through the near addition portion of the spectacles for near work cannot be guaranteed. And this is particularly so when dealing with children. The bifocal contact lenses that have been used to date have been simultaneous vision bifocals—i.e. both the distance and the near images are produced in the eye simultaneously. Such bifocals degrade the overall retinal image quality and are known to produce undesirable visual problems such as haloes, glare and ghosting.

Yet other optical methods seek to reduce the progression of myopia by manipulating the aberrations in the visual image introduced to the eye. "Aberrations" refers to the optical performance characteristic of an optical lens or system that relates to how poorly a visual image is produced by that lens or system. When a visual image is formed perfectly sharply or distinctly (relative to the limits of diffraction which is an ultimate physical limit of how sharply a focus can be produced) and in the required location in space, the image is said to be free of aberrations. With departure from this perfect state, the visual image is said to suffer from aberrations. It is thought by some that certain aberrations can influence the progression of myopia.

A few optical methods relating to the manipulation of on-axis (or axial) optical performance of the vision device, or its on-axis aberrations, have been developed for the treatment of myopia progression. "On-axis" or "axial" is a description of the direction of light relative to the direction of vision. The most visually acute point on the retina (the light-sensing layer of the eye) is the fovea. This is a small area on the retina at which the light-sensitive photo-receptors are at their highest concentration. When an individual needs to critically view a visual object, he does so by changing the direction of gaze (by rotation of the head or rolling of the eyeball up/down, left/right) so that the point of interest in the image is placed over the fovea of the eye. This process of aligning the eye's most sensitive point to the visual object of interest is called "fixation". "On-axis" or "axial" refers to when light arriving to the eye originates from the point in the visual object which is imaged on to the fovea, i.e. the point of fixation, or in the straight-ahead direction. In this situation, the light rays arriving to the eye are approximately parallel to the axis of the eye.

For example, U.S. Pat. No. 6,045,578 to Collins discloses a method of treatment and prevention of myopia by inducing positive spherical aberration (an on-axis aberration) in the myopic eye. US 2003/0058404 to Thorn describes a method of measuring and correcting the wave-front aberrations of parallel light rays entering the eye in order to prevent or retard the progression of myopia. US 2004/0237971 to Radhakrishnan describes the manipulation of aberrations to control the relative position of modulation transfer function peaks in order to retard or abate the progression of myopia.

The general efficacy of the manipulation of on-axis optical methods is yet to be definitively proven. In at least some of the on-axis optical methods described (for example, the induction of positive spherical aberration), the method necessarily implicitly degrades the visual acuity and could lead to poor compliance on the part of the patient and would therefore suffer the same disadvantages as under-correction methods.

In contrast to these optical methods which deal with the manipulation and control of optical focus and aberrations in the straight-ahead, on-axis direction, the disclosure of U.S. Pat. No. 7,025,460 demonstrated that myopia progression is controlled by the off-axis optical characteristics. Converse to on-axis, "off-axis" refers to when light is arriving to the eye from a direction other than straight-ahead; i.e. the image points corresponding to the off-axis object points lie away from the fovea. Off-axis visual direction is also referred to as "peripheral vision" and the object points (points in the visual scenery) belonging to the off-axis direction the "peripheral visual field" or simply "peripheral field". When light arrives to the eye from an off-axis direction, it creates an angle with the straight-ahead direction of view of the eye. This angle is sometimes called the "field angle".

U.S. Pat. No. 7,025,460 describes a set of experiments and observations that demonstrate that retarding or eliminating eye-growth that leads to progression of myopia may best be effected by controlling the peripheral visual image. From those observations, U.S. Pat. No. 7,025,460 teaches an optical method for treating the progression of myopia by manipulating the positions of peripheral (i.e. off-axis) visual image points, or the relative curvature of field of the visual image.

It should be mentioned that curvature of field is the type of off-axis optical aberration that relates to the antero-posterior position (i.e. whether further in front of, or further behind) of the peripheral image points (of the visual image) relative to the preferred image-receiving surface (which in the eye, is the retina). Curvature of field differs fundamentally from spherical aberration (for example as taught by U.S. Pat. No. 6,045,578 and US 2003/0058404). Spherical aberration is the optical aberration that describes whether light rays, all from the same straight-ahead (along the visual axis) direction, but passes through different points on the pupil of the eye, are focused to the same image point. Thus spherical aberration relates to how well (or sharply) an image point from its corresponding object point from the straight-ahead direction is focused whereas curvature of field relates to where in space (antero-posteriorly or forward-backward position-wise) image points from many different directions (i.e. from different field angles) in the visual scenery is positioned regardless of how sharply they are focused. The set of all such image points can be described as an image surface. So curvature of field relates to the shape and position of the image surface.

In comparison, it should also be noted that the bifocal optical methods (for example, as taught by U.S. Pat. No. 6,752,499) seeks to create two image points for each visual object point (this is a feature of simultaneouos vision bifocal contact lenses). Thus, 'double image' is implicitly created—one from the near focus zone and one from the distance focus zone of the bifocal. In comparison, the control of curvature of field creates only a single image point for each visual object point but governs the antero-posterior position of the image point relative to the image-receiving surface.

One aspect of U.S. Pat. No. 7,025,460 is a method of designing a vision treatment device (for example, contact lens, spectacle lens, corneal inlay or onlay, etc.) to be worn by a wearer that will manipulate the positions of the peripheral image points (that is, manipulate the relative curvature of field) in such a way so as to produce stimuli to reduce or eliminate the progression of myopia in the wearer while simultaneously maintaining the position of the on-axis visual image point on the retina/fovea so as to maintain good visual acuity for the wearer.

Designing a vision treatment device according to the teachings of U.S. Pat. No. 7,025,460, depending on the exact shape of the image surface (i.e. relative curvature of field) to be presented to the eye, may require some trade-off between the manipulation of relative curvature of field and the amount of other optical aberrations that results. Since most conventional optical vision correction devices have typically only two (one anterior, one posterior) optical surfaces, when the lens is designed to manipulate relative curvature of field, due to the limited number of design parameters (e.g. lens surface shape, refractive index of material, lens thickness, distance from the pupil, etc) limiting the degrees of freedom in optical design, some other optical aberrations may be concomitantly introduced or altered. Such other optical aberrations (i.e. aberrations other than curvature of field), may be described according to the von Seidel classification of aberrations as is well-known to those skilled in optics and lens design. These include spherical aberration (which has already been described above) as well as coma, oblique astigmatism and distortion. Throughout this document, we will refer to these as the "other optical aberrations".

One other category of aberration is the chromatic aberration. This aberration is related to how light of different colors (wavelengths) creates different focal positions and does not impact on the concept and applicability of the present invention.

In terms of other optical aberrations, vision optical devices can be divided roughly into two groups according to whether they remain substantially approximately aligned with the direction of view of the eye with different directions of gaze of the eye.

Vision correction devices of the first group can be called "centered" vision correction devices and include contact lenses, intra-ocular lenses, on-lays, in-lays and anterior chamber lenses. The optical axis of these vision correction devices remains substantially approximately aligned with the direction of view of the eye regardless of its direction of gaze. For the centered vision correction devices, light from the on-axis visual object always passes approximately through the central region of the device on its way to the fovea after passing through the pupil of the eye.

Vision correction devices of the second group can be called "decenterable" vision correction devices and include spectacles and translating-type (e.g. translating bifocal) contact lenses. Devices in this group do not remain aligned with the direction of view of the eye depending on the direction of gaze of the eye.

For centered vision correction devices, undesirable other optical aberrations may arise through the portion of the optical device that corresponds to the off-axis directions or peripheral fields in the manner described above. This also applies to the decenterable vision correction devices when the eye is in the straight-ahead gaze position with the direction of vision passing through or near the optical center of the device.

For decenterable vision correction devices, the other optical aberrations produced by the periphery of the optical device may also impact foveal vision. This occurs when the eye is not in straight-ahead gaze. When the eye is in the straight-ahead gaze, the line of sight of the eye passes through the device at what is called the "distance visual point". Typically, except for certain special applications, for best visual performance, the distance visual point is placed near or at the optical center of the device. When the eye is rotated away from straight-ahead gaze, it will no longer be looking through the center of the device. In those "eccentric" directions (i.e. a direction of gaze not in the straight-ahead direction) of gaze, the image produced on the foveal region will be constructed from light rays that pass through a peripheral portion of the device. Such an image will incur and suffer from the other optical aberrations produced by the peripheral portion of the device.

In addition to the undesirable other optical aberrations produced by the peripheral portion of the device, decenterable vision correction devices that employ the myopia treatment method as taught by U.S. Pat. No. 7,025,460 can also suffer from blurring due to defocus during eccentric gaze. The repositioning of peripheral focal points for retarding the progression of myopia as taught by U.S. Pat. No. 7,025,460 implicitly introduces defocus to the peripheral image. While this is a desirable characteristic in terms of retardation of myopia progression when the eye is in the straight-ahead gaze, when the eye is in eccentric gaze, the image produced on the foveal region is produced by rays passing through a peripheral portion of the device and therefore will incur an amount of defocus. Thus, when the eye is directed to fixate on a peripheral visual object through a decenterable visual correction device, the image is blurred due to both defocus and other optical aberrations.

Such other optical aberrations (and also defocus in the case of decenterable vision correction devices during eccentric gaze) may be sufficiently, relatively, small in amount that vision remains acceptable to the wearer (who would be enjoying the benefit of producing a stimulus to retard or eliminate the progression of myopia and therefore may, in preference, be prepared to compromise on certain aspects of visual performance). However, other wearers may require certain select zone or multiple zones for which vision is critically important, and therefore a priority. Such zones, which will be called "vision priority zones" in this document, represent zones on a lens that correspond to particular visual directions (i.e. visual field direction or angles) for which the wearer requires good vision.

A few examples follow to illustrate when a wearer may choose to have a vision priority zone on their vision correction devices and where these associated vision priority zones may be located on the device.

In one example, a wearer may be engaged in driving a vehicle and requires not only good vision in the straight-ahead (on-axis) direction (as is provided by the method of U.S. Pat. No. 7,025,460) but also useful vision along a horizontal line representing a visual "sweep" of many visual objects (at many directions of gaze) lying on or across a roadway. Since the task of driving requires the wearer to primarily be visually aware along a horizontal line (e.g. to check for traffic in the cross street at a junction), the select vision priority zone for which useful vision is required would be represented by a band lying in a horizontal line. It should be noted that useful vision in the context of peripheral vision is a relative term since the density of photo-receptors on the retina decreases away from the fovea; hence there exists a physiological limit to visual acuity at the peripheral retina which decreases away from central, foveal vision.

In another example, the wearer may be engaged in a visual task which requires acute recognition and identification of fine visual objects in an extended central field (i.e. the region immediately surrounding the straight-ahead direction). Examples of such tasks may include radar operation for which the operator is required to view a radar screen or computer monitor and quickly detect and identify small points. For such wearers, the expanse (i.e. area or field of vision) of good on-axis and 'nearly' on-axis (a region peripheral to but near the central point also called the "para-central" region) visual acuity offered by the method according to U.S. Pat. No. 7,025,460 may be insufficient and a vision priority zone providing a wider para-central zone of good vision may be beneficial. The select zone of vision for this example may be a region approximately centered on the visual axis which subtends a field of view approximately equal to the size of the visual task (e.g. a computer monitor, a radar display unit, a musician's score, an artist's easel, an architect's drafting board, etc).

In yet another example, when a wearer of a decenterable vision correction device (such as a pair of spectacles) is reading, both eyes tend to point downward and converge (i.e. point slightly closer towards the direction of the nose). In this direction of gaze, each eye is looking through a point of the device that is positioned relatively lower and more "nasally" (a term used by eye-care practitioners to indicate a direction towards the nose—i.e. leftward for the right eye and rightward for the left eye) than the distance visual point. This point is called the "near visual point". Thus for the case of a decenterable vision correction device, a wearer who is engaged for long periods in reading tasks (for example clerical work, book proof-reading, fine-arts such as engraving, embroidery) may require, in addition to good on-axis vision through the centre of the device, a select vision priority zone at the near visual point that provides good visual acuity. The useful size of the vision priority zone at the near visual point will depend on the size of the near work material (e.g. book page, artwork, etc). Given the foregoing, it would be desirable to provide further improvements in methods and visual treatment devices for the retardation or cessation of progression of myopia.

SUMMARY OF THE INVENTION

Embodiments of the present generally relate to methods and devices for the retardation or cessation of refractive error progression. The over-arching approach involves 1) the repositioning of the peripheral image to provide stimulus to retard or eliminate the progression of myopia or hyperopia and 2) maintaining good central vision by positioning the central image on or near the fovea/retina, while 3) substantially simultaneously providing one or more vision priority zones, for select visual directions, with controlled or reduced defocus and/or other optical aberrations to provide good, useful vision at those select directions. The devices for the delivery of this method may include, but are not limited to, spectacles, contact lenses (including those used for orthokeratology, corneal on-lays, corneal in-lays, anterior chamber lenses, intra-ocular lenses), etc. Preferred methods may involve techniques including but not limited to corneal refractive surgery (e.g. photorefractive keratectomy, LASIK, LASEK), orthokeratology, etc.

An embodiment of the invention relates to a method of retarding the progression of myopia by providing to the eye a stimulus to retard or cease the progression of myopia by repositioning the peripheral visual image (from off-axis visual object points when the eye is in the straight-ahead viewing direction of gaze) so that at least the more anterior of the two image surfaces associated with astigmatism is positioned on, or anterior to, the retina, while substantially simultaneously providing good central vision to the eye by positioning the central visual image (from on-axis visual object points when the eye is in the straight-ahead viewing direction of gaze) so that the image lies near to or on the fovea of the eye; and also substantially simultaneously providing one or more vision priority zones corresponding to select directions of fixation for the eye, for which other optical aberrations and/or defocus is controlled or reduced to provide to the eye good, useful vision along those select directions of fixation.

One preferred configuration for an optical vision treatment device (e.g. spectacle lens, contact lens, corneal in-lay or on-lay, intra-ocular lens, anterior chamber lens, etc) that may be used in the delivery of the above methods comprises a vision treatment zone over a substantial area of the device whereby the optical design within the vision treatment zone is manipulated so that peripheral visual images formed by the vision treatment device in combination with the optics of the eye is repositioned in a way that, at least the more anterior of the two image surfaces associated with astigmatism is positioned on or anterior to the retina, while the central visual image formed by the vision treatment device in combination with the optics of the eye is positioned near to or on the fovea of the eye when in straight-ahead gaze. Accompanying the vision treatment zone of the optical vision treatment device is added at least one vision priority zone, whereby the optical design within the vision priority zone(s) is manipulated so that, in combination with the optics of the eye, the visual images belonging to the direction(s) of gaze associated with the vision priority zone(s) are formed with controlled or reduced amounts of other optical aberrations and/or defocus.

In another embodiment of the invention, at least one vision priority zone of the vision treatment device is directed to provide good, useful para-central vision whereby the vision priority zone has an extent at least substantially equivalent to approximately the size of the pupil of the eye projected onto the position of the device, but is preferably chosen to match the size of the visual object of the wearer. Such a visual object may include, but not be limited to, computer monitors, televisions, book pages, letter-size paper, music score, etc.

In yet another embodiment of the invention, at least one vision priority zone of the vision treatment device is directed to provide good, useful vision along a line/band (representing a "sweep" of a range of directions of gaze) of choice, whereby the vision priority zone describes a band that extends partially or entirely across the device along—the line/band, and the height of the vision priority zone band is at least substantially equivalent to approximately the size of the pupil of the eye projected onto the position of the device, and the optical design within the vision priority zone band is manipulated so that, in combination with the optics of the eye, the visual images belonging to the direction(s) of gaze along the line/band are formed with controlled or reduced amounts of other optical aberrations and/or defocus.

In still yet another embodiment of the invention, at least one vision priority zone of the vision treatment device is directed to provide good, useful vision at a near visual point whereby the position of at least one of the vision priority zones on the vision treatment device is chosen to coincide with the near visual point of the device that lies on a line joining the eye to the near visual object, with the vision priority zone having an extent at least equivalent to approximately the size of the pupil of the eye projected onto the position of the device, but may preferably be chosen to substantially match the size of the near visual object of the wearer. Such a near visual object may include, but is not limited to wrist watches, personal digital assistants, mobile phones, book pages, letter-size paper, music score, etc., with the optical design within the vision priority zone manipulated so that, in combination with the optics of the eye, the visual images through the vision priority zone are formed with controlled or reduced amounts of other optical aberrations and/or defocus.

In still yet another embodiment of the invention, at least one vision priority zone of the vision treatment device is directed to provide good, useful vision at visual points between the straight-ahead direction of view, through intermediate viewing distances, to a near point whereby the vision priority zone on the vision treatment device describes a band extending from the distance visual point of the device to the near visual point of the device, and the vision priority zone has a width at least substantially equivalent to approximately the size of the pupil of the eye projected onto the position of the device, but may preferably be chosen to match the size of the intermediate or near visual objects of the wearer. Such intermediate and near visual objects may include but are not limited to wrist watches, personal digital assistants, mobile phones, book pages, letter-size paper, computer monitors, display units, music score, etc.

Given the foregoing, it will be clear that multifunctional devices may be constructed involving combinations of vision priority zones of different configurations that are incorporated in the one vision treatment device to accompany the underlying vision treatment zone, in order to reduce or cease the progression of refractive error, provide good central vision and provide good, useful vision through select vision priority zones.

It will also be clear from the foregoing that the method may be applied to retarding the progression of hyperopia by providing to the eye a stimulus to retard or cease the progression of hyperopia by repositioning the peripheral visual image (from off-axis visual object points when the eye is in the straight-ahead viewing direction of gaze) so that at least the more posterior of the two image surfaces associated with astigmatism is positioned on or posterior to the retina, while simultaneously providing good central vision to the eye by positioning the central visual image (from on-axis visual object points when the eye is in the straight-ahead viewing direction of gaze) so that the image lies near to or on the fovea of the eye, and also simultaneously providing one or more vision priority zones corresponding to select directions of fixation for the eye for which other optical aberrations and/or defocus is controlled or reduced to provide to the eye good or useful vision along those select directions of fixation.

These and other objects and advantages of the invention will be further apparent in consideration of the drawings and the detailed description of the preferred embodiments, and in view of the appended claims defining the invention.

BRIEF DESCRIPTION OF THE DRAWINGS

The accompanying figures illustrate aspects of the invention and embodiments of the present invention. These, together with the description, explain the objects, advantages and principles of the invention. In the figures:

FIG. 8a is a vision correction device placed on an eye in its straight-ahead gaze direction;

FIG. 8b shows the vision correction device of 8A placed on the same eye but with the eye in a downward gaze direction;

FIG. 8c is a curvature of field plot showing the image surface of the eye and vision correction device of 8A and 8B in combination in relation to the foveal sphere;

FIG. 9A is the front-on design layout of a vision treatment device showing the placement of a vision priority zone band that includes the optical center of the vision treatment device;

FIG. 9B is a relative curvature of field plot of the example device in FIG. 9A along a meridian containing the vision treatment zone;

FIG. 9C is a relative curvature of field plot of the example device in FIG. 9A along a meridian containing the vision priority zone.

FIG. 11A is the front-on design layout of the vision treatment device showing the placement of a vision priority zone region that includes the near visual point of the vision treatment device;

FIG. 11B is a relative curvature of field plot of the example device in FIG. 11A along a meridian containing the vision treatment zone;

FIG. 11C is a relative curvature of field plot of the example device in FIG. 11a along a meridian containing the vision priority zone;

FIG. 12A is the front-on design layout of the vision treatment device showing the placement of a vision priority zone region possessing relative positive power at the near visual point of the vision treatment device;

FIG. 12B is a relative curvature of field plot of the example device in FIG. 12A along a meridian containing the vision treatment zone; and FIG. 12C is a relative curvature of field plot of the example device in FIG. 12A along a meridian containing the vision priority zone.

DETAILED DESCRIPTION OF THE INVENTION

For the wearers, such as those described in the previous sections, who require good central vision as well as certain select other directions of gaze, it would be beneficial and advantageous to provide a vision treatment device that can impart the refractive error-reducing stimulus through the appropriate manipulation of the position of the peripheral image points as taught by U.S. Pat. No. 7,025,460, but for which other optical aberrations are reduced for those select directions of gaze—i.e. for the vision priority zones. In addition, should the vision treatment devices be of the decenterable type, it would be beneficial and advantageous to not only control or reduce the other optical aberrations through the select directions of gaze but also to control or reduce defocus.

Figure 1:
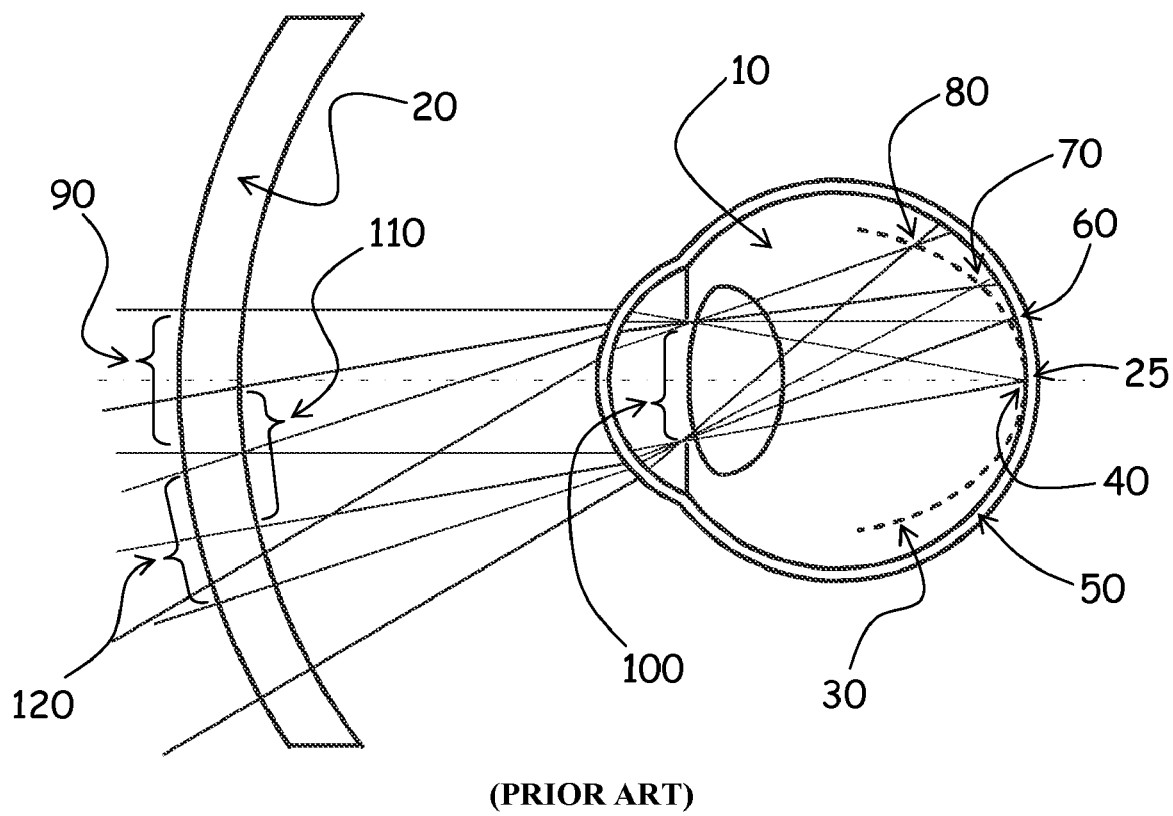
FIG. 1 is a diagram of an eye with a vision treatment device of the prior art designed to reduce myopia progression by the control of curvature of field, illustrating the role a finite pupil size plays on the impact of other optical aberrations on the visual image quality.

FIG. 1 explains the rationale pertaining to the control of other optical aberrations behind the current invention. In FIG. 1, an eye 10, with myopic tendencies (i.e. is either myopic or would develop myopia) is treated with a lens 20, using the method as taught by U.S. Pat. No. 7,025,460, so as to retard or eliminate the progression of myopia in this eye. In this particular example, the lens 20, has been designed to deliver a negative relative curvature of field (per U.S. Pat. No. 7,025,460) effective from immediately outside or peripheral to the region of the fovea 25, of the eye 10 (the "fovea" is the region of the retina 50 with the highest visual acuity and is used for critical vision). This results in an image surface 30, for which the central, axial image point 40, is focused on to the fovea 25 enabling good central focused vision while simultaneously placing the peripheral image points 60, 70, 80 in front of the peripheral retina 50 thus reducing or eliminating the stimulus for eye growth and effectively retarding or eliminating myopia development or progression.

Figure 2:
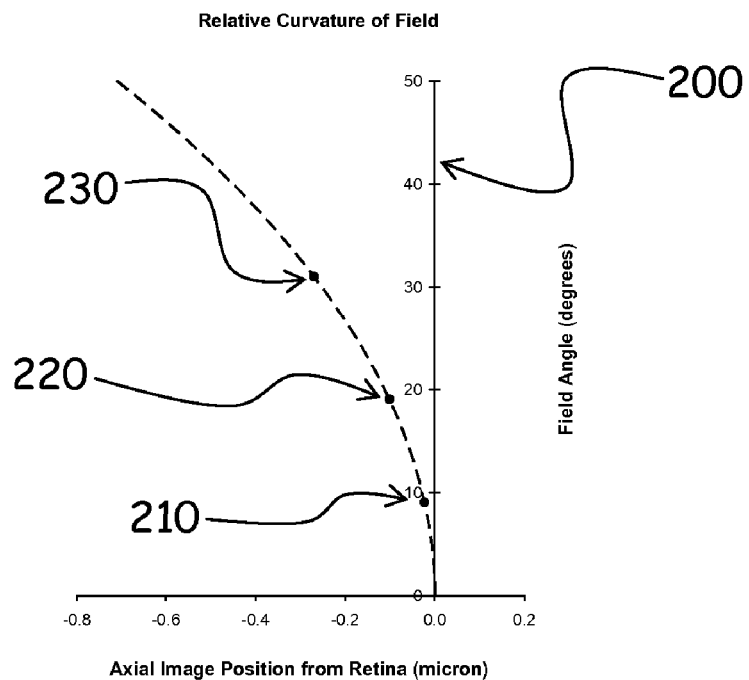
FIG. 2 is a relative curvature of field plot of the image surfaces of the prior art combination of the eye and vision treatment device shown in FIG. 1.

The relative curvature of field graph for the example of FIG. 1 is shown in FIG. 2. In a relative curvature of field graph, the anatomically curved retinal surface is 'remapped' as a vertical straight line 200. The remapping retains the axial distance (i.e. distance measured antero-posterior or in the forward-backward direction approximately parallel to the direction of light in the eye) of the image surface from the retina. Thus, a negative field curvature will be seen as a line that is approximately 'concave' to the left averaged over its length. It can be seen that for the design in the example of FIG. 2, all peripheral image points 210, 220, 230—including those immediately peripheral to the fovea (i.e. the para-central points)—lies to the left (i.e. in front) of the retina 200 thus offering a negative relative curvature of field.

It is known to lens designers that given the few degrees of freedom in optical design of a vision correction lens (i.e. having typically only two optically refractive surfaces—one front surface, one back surface), when a lens is designed to control curvature of field, it cannot simultaneously also control, or in particular optimize, other optical aberrations (such as coma, distortion and astigmatism). For example, the effect of oblique astigmatism (a type of off-axis aberration also called "radial astigmatism") is to produce two separate sharp line foci instead of a single sharp point focus. (Note that the aberration oblique astigmatism differs from that of refractive astigmatism. The former relates to an aberration that creates two line foci caused by light traveling in an off-axis direction through an optical system. The latter refers to the creation of two line foci in foveal refraction that affects the vision of the eye. Throughout this document, unless otherwise indicated, "astigmatism" shall refer to the "oblique astigmatism" aberration). The presence of astigmatism as a consequence of controlling curvature of field can be seen in the relative curvature of field graphs disclosed in U.S. Pat. No. 7,025,460, which is incororated by reference herin as if made a part of the present specification. In the relative curvature of field graphs of U.S. Pat. No. 7,025,460, two line foci are shown, one labeled "S" for the sagittal line focus and the other "T" for the tangential line focus. The further apart these two line foci are, the greater is the amount of astigmatism. The result of astigmatism and the other optical aberrations is poorer vision for the peripheral visual directions. The manipulation of curvature of field therefore implicitly also potentially degrades visual image in the periphery—progressively increasing in magnitude from the para-central to the far peripheral regions.

The impact of other optical aberrations is associated with the pupil size of the eye. Resuming on FIG. 1, because the pupil 100 of the eye (and therefore the projected entrance pupil 90 of the eye) has a finite size, it can be seen that each location on the lens 20 may be involved in the refraction (i.e. focusing) of light for more than one image point. (In visual optics terminology, the 'dark circle' of the eye which is commonly called the "pupil" by the lay-person is in actuality the "entrance pupil" of the eye as it is the image of the physical pupil created by the opening in the iris, magnified by the front of the eye—i.e. the cornea, and any other optical devices between the iris and the observer—that is seen by the observer). For example, light rays traveling to the central-field image point 40, would pass through a central-field optical region on the lens 20 that corresponds to the projected entrance pupil 90 (the "projected entrance pupil" is the size and edge outline of the pupil projected forward onto the lens) of the eye. Thus, any changes in the optical design of the lens within this region 90 would affect how light is focused to the foveal region.

However, it can be seen that light rays traveling to the peripheral image point labeled 60 would pass through an optical region 110 on the lens 20 somewhat peripheral to, but overlapping with, the central-field optical region 90. The overlapping of these two optical regions 90 and 110 means that any attempt to modify the optical design of the lens 20 to effect a change in relative curvature of field to place the peripheral image point 60 more anteriorly than the retina 50 could introduce some form of other optical aberrations to the central image point at 40. Similarly, the overlapping of peripheral optical regions 110 and 120 means that any attempts to control relative curvature of field to place the peripheral image point 70 more anteriorly than the retina 50 would introduce some amount of other optical aberrations to the peripheral image point at 60.

The amount of overlap of optical regions on lens 20 between peripheral image points and the central image point 40 decreases as the field angle of the peripheral image point increases (i.e. progressively for peripheral image points 60, 70, 80). There will be a peripheral image point 70, for which the field angle is sufficiently large that there is no effective optical overlap of its associated peripheral-field optical region 120 on the lens 20 with the central-field optical region 90. This occurs when the projected entrance pupil at the two field angles (for central and peripheral field) do not overlap significantly.

For image quality not to be degraded at select visual direction(s) from the para-central to the far peripheral region of a lens, the control of curvature of field for those select visual direction(s) will need to be moderated or removed. This may be done at select optical regions on the visual treatment device. This approach forms a basis of the current invention.

Figure 3:
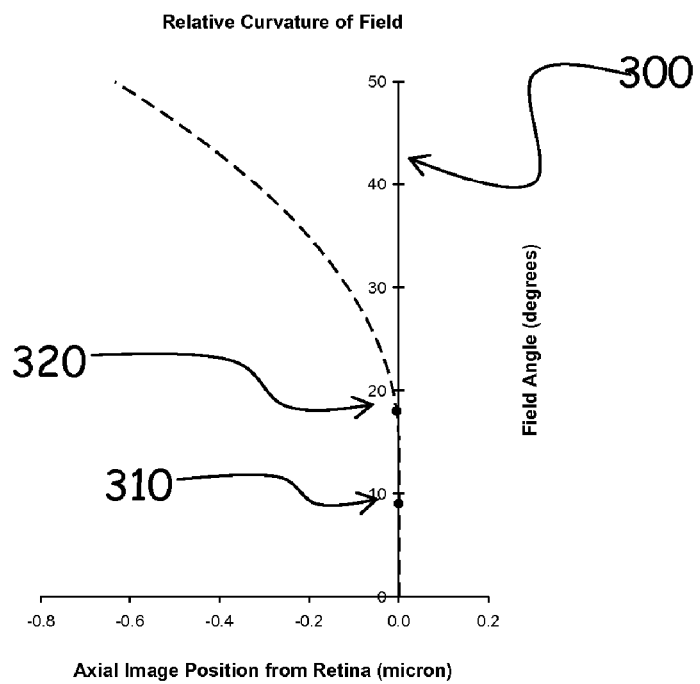
FIG. 3 is a relative curvature of field plot of the image surfaces of the eye and a vision treatment device method of one embodiment of the present invention.

Therefore, one embodiment of the present invention relates to a method to begin introducing optical design for providing the appropriate relative curvature of field or peripheral focusing, suitable for retarding or eliminating myopia progression (i.e. the vision treatment zone), at the lowest peripheral field-angle for which there is no significant overlap of the projected entrance pupil with the central (axial) field. This lowest peripheral field-angle will be called the "starting design field-angle". The resultant effect on relative curvature of field is illustrated in FIG. 3. It can be seen in the relative curvature of field graph of FIG. 3 that there is no attempt to control relative curvature of field (which therefore will remain in its 'conventional' state; and may be negative, positive or neutral according to other design requirements for the lens—in FIG. 3, it is illustrated by way of example only as neutral—i.e. the image surface within this region lies close to or on the retina) in the para-central fields (for example near-peripheral image point 310 lies on the retina 300). Relative curvature of field control (provided by the vision treatment zone) is introduced at the "starting design peripheral image point" 320 which corresponds to the starting design field-angle for which the projected entrance pupil size along the direction of the starting design field-angle no longer overlaps significantly with the central-field optical region. All image points more peripheral to the starting design peripheral image point 320 are focused substantially on or in front of the retina 300 to remove stimulus for eye-growth for those peripheral-field regions of the retina.

Figure 4:
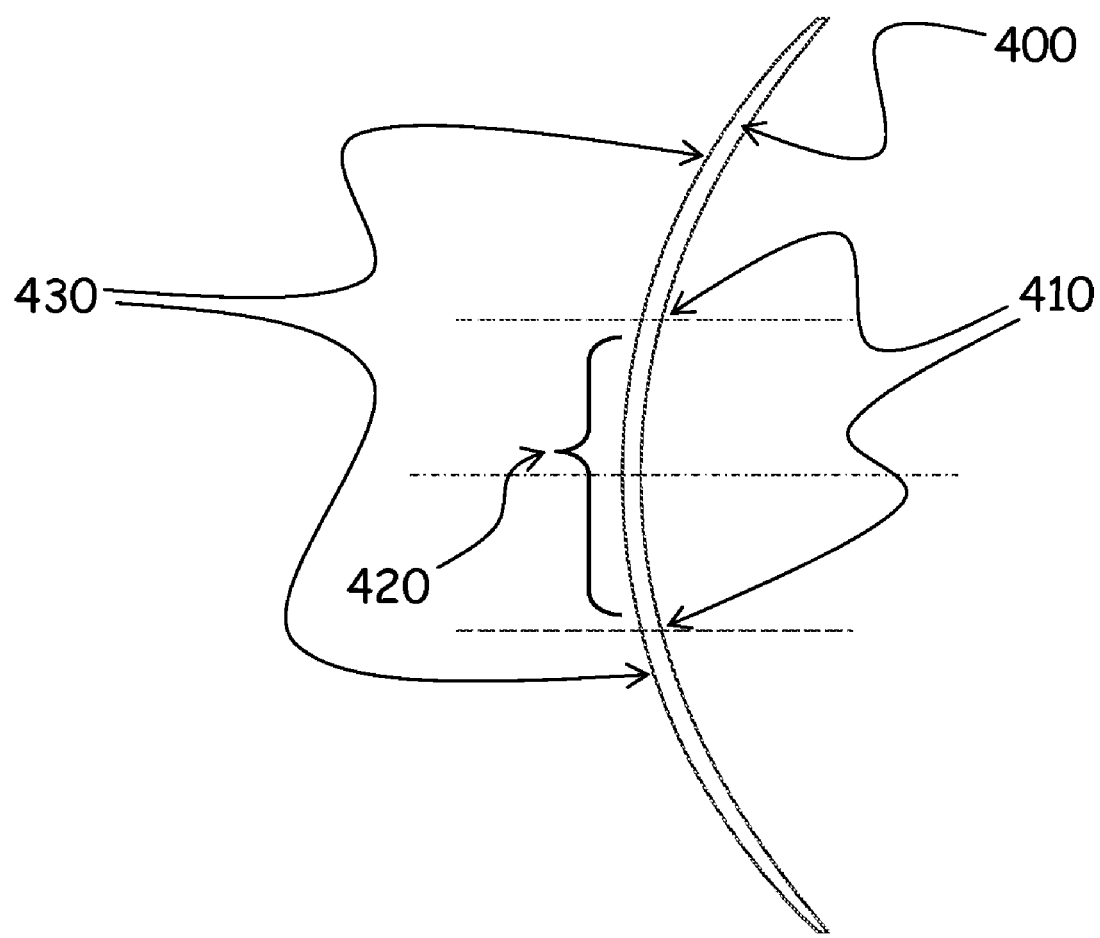
FIG. 4 is a profile of an one embodiment of an optical vision treatment device of the present invention showing the location of the central optical region providing a vision priority zone and the location from where curvature of field control for reduction of myopia progression commences.

In terms of the design with respect to the lens 400 as illustrated in FIG. 4, this translates to the introduction of appropriate relative curvature of field in the design beginning at a distance 410 just outside the central-field optical region 420 (being at least approximately the size of the projected entrance pupil). Within the central-field optical region 420, relative curvature of field or peripheral focusing design is not substantially applied, thereby avoiding the introduction of other optical aberrations. This central-field optical region 420 therefore represents a zone of improved visual performance useful for wearers who require good vision within this zone. This central-field optical region 420 therefore represents one form of a vision priority zone. While outside the central optical region 420, beyond the starting design peripheral point 410, control of relative curvature of field or peripheral focusing is incorporated (by the vision treatment zone 430 of the device 400). In so doing, we will be reducing or eliminating the stimulus for eye-growth while also not introducing additional other optical aberrations to the central-field optical region used most frequently for critical distance viewing.

The exact size and position of this central-field optical region is determined by a number of parameters that includes the refractive state of the eye, the refractive power of the lens, the vertex distance (i.e. distance from the lens to the eye) and the size and edge or outline of the entrance pupil of the eye. Thus, for optimal design, the above parameters should be established for individual wearers. However, when designing for volume production of lenses, an acceptable 'population' average may be used for those parameters to arrive at a workable 'typical' distance central-field optical region size.

It should be noted that it is not required for the central-field optical region and the projection of the entrance pupil at the starting design field angle to have no (i.e. zero amount of) overlap. It is only necessary for there to be no significant overlap. Due to the existence of the Stiles-Crawford effect well-known to experts in visual optics, light rays passing nearer the edge of the pupil contribute effectively far less to the visual image than light rays passing nearer the center of the pupil. Physiologically, light rays which pass through the pupil near its edge evoke a lesser visual signal to the visual cortex than light rays that pass through the pupil near its center. Thus blur caused by light rays passing through the pupil near its edge is much less noticeable to the eye than blur caused by light rays passing through the centre of the pupil. Therefore, a small amount of overlap of the central-field optical region at the central and the projections of the entrance pupil at the starting design field angle, which would allow only light rays close to the edge of the pupil to pass through and, which contribute insignificantly to the visual image can be acceptable visually to the wearer and also permit the control of peripheral focusing (by the vision treatment zone) to begin nearer the center of the lens, thereby providing a greater area of the vision treatment zone contributing to the stimulus for reducing myopia progression.

It may be preferable in some instances to provide for a larger central-field optical region than that corresponding to approximately the projected entrance pupil of the eye as described above. The wearer may require good vision for a larger field of view over which the presence of other optical aberrations does not degrade the visual image unacceptably—i.e. a vision priority zone. Examples of when larger vision priority zones may be required include wearers working on monitors (e.g. computer screens, radar display units), musicians reading scores, artists painting on easels, architects on drafting boards, etc. For each of these applications, the required size of the vision priority zone (corresponding to the desired para-central field optical region on the lens) may be calculated by considering the trigonometry of the vertex distance of the optical device, the entrance pupil size, the working distance and the size of the work surface (e.g. US Letter page size, computer screen size, canvas size, etc) as understood by those skilled in the art.

Thus, the starting design optical region, that defines a para-central vision priority zone, beyond which curvature of field control commences, may be approximately equal to or larger than the projected entrance pupil of the eye according to the visual needs of the wearer.

While the lens provided in the example illustrated by FIGS. 1 to 4 is in a form analogous to a spectacle lens, it should now be immediately clear to those skilled in the art that the foregoing is similarly applicable to other optical devices including but not limited to contact lenses, corneal in-lays and on-lays, anterior chamber lenses and intra-ocular lenses. It is also applicable to the design and profiling of corneal surfaces in treatments such as photorefractive keratectomy (PRK), laser in-situ keratomileusis (LASIK) and other refractive surgical treatments, etc.

It also will be immediately clear to those skilled in the art, given the above description of the current invention, that the central optical region may be 'left alone' (i.e. unmodified or without relative curvature of field control) or that additional optical design features may be incorporated to this region such as the inclusion of correction for the aberrations of the eye in the central, straight-ahead viewing direction. Other additional features relating to the central optical region are possible and will become obvious to the optical designer given this disclosure.

Figure 5:
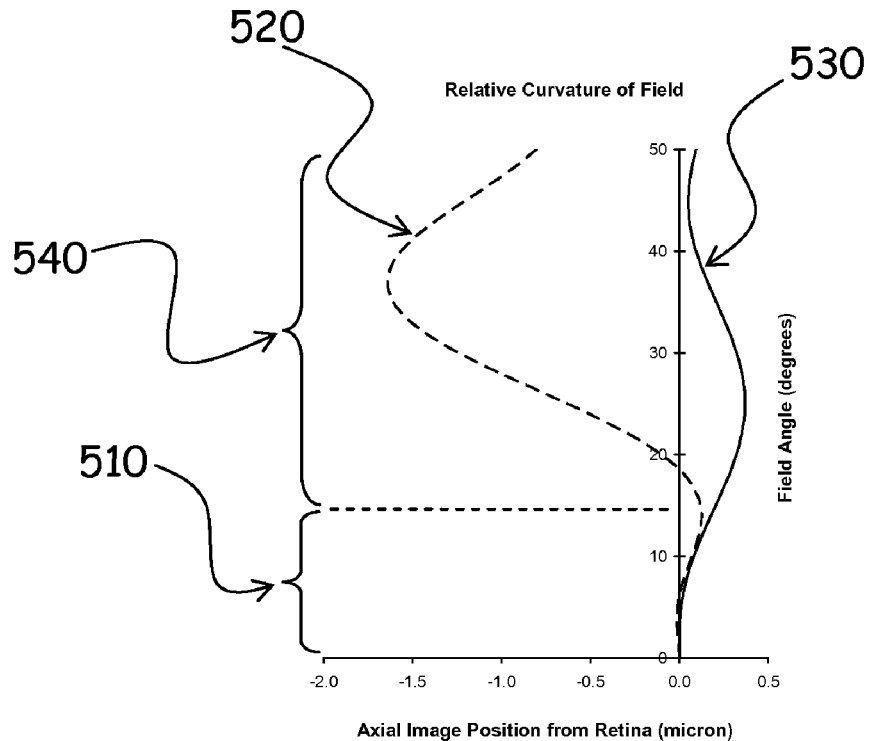
FIG. 5 is a relative curvature of field plot of an example contact lens for reducing progression of myopia by controlling the position of peripheral focal points that incorporates a para-central vision priority zone with effectively no spherical aberration.

Given the above design methods, it should now be clear to lens designers how specific designs may be achieved using lens design techniques known to those skilled in the art. However, by way of illustration, FIG. 5 shows the relative curvature of field plot of a contact lens designed to treat a −3.00D myope. In this contact lens design, astigmatism has been significantly reduced within the vision priority zone 510 as can be seen by the proximity of the two line foci 520 and 530 associated with astigmatism within this zone. Beyond the vision priority zone 510, the vision treatment zone 540 begins and employs the control of curvature of field to reduce the progression of myopia as can be seen by the positioning of the more anterior 520 of the two line foci 520 and 530 of astigmatism to be more anterior to the retina. This control of curvature introduces the secondary effect of astigmatism as can be seen by the separation of the two line foci 520 and 530 in the vision treatment zone 540. It can also be seen that spherical aberration has been practically eliminated in the central-field optical region (i.e. within the vision priority zone 510) while beyond the central-field optical region, relative curvature of field (i.e. focus of peripheral focal points) has been manipulated to produce a stimulus to retard the progression of myopia.

Figure 6:
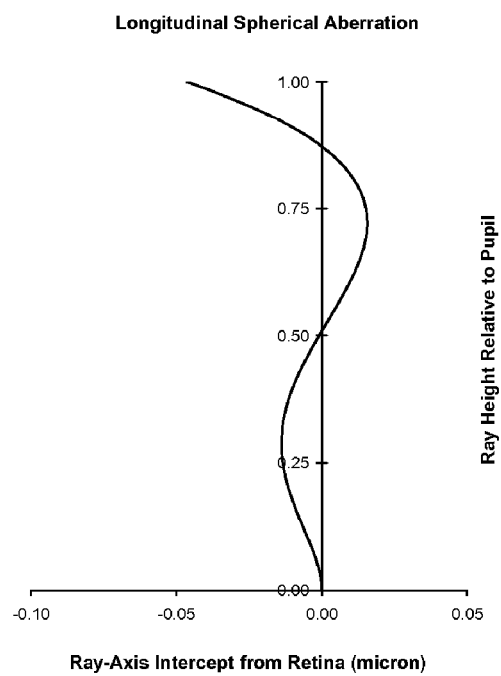
FIG. 6 is a longitudinal spherical aberration plot of the example contact lens of FIG. 5.

FIG. 6 shows the longitudinal spherical aberration of this contact lens within the pupillary region, being much less than 100 nanometers—i.e. spherical aberration has been practically eliminated from this lens. This contact lens, therefore, will not introduce significant additional spherical aberration to the eye and would afford the eye excellent central on-axis vision while also providing a treatment effect for reducing progression of myopia.

Figure 7:
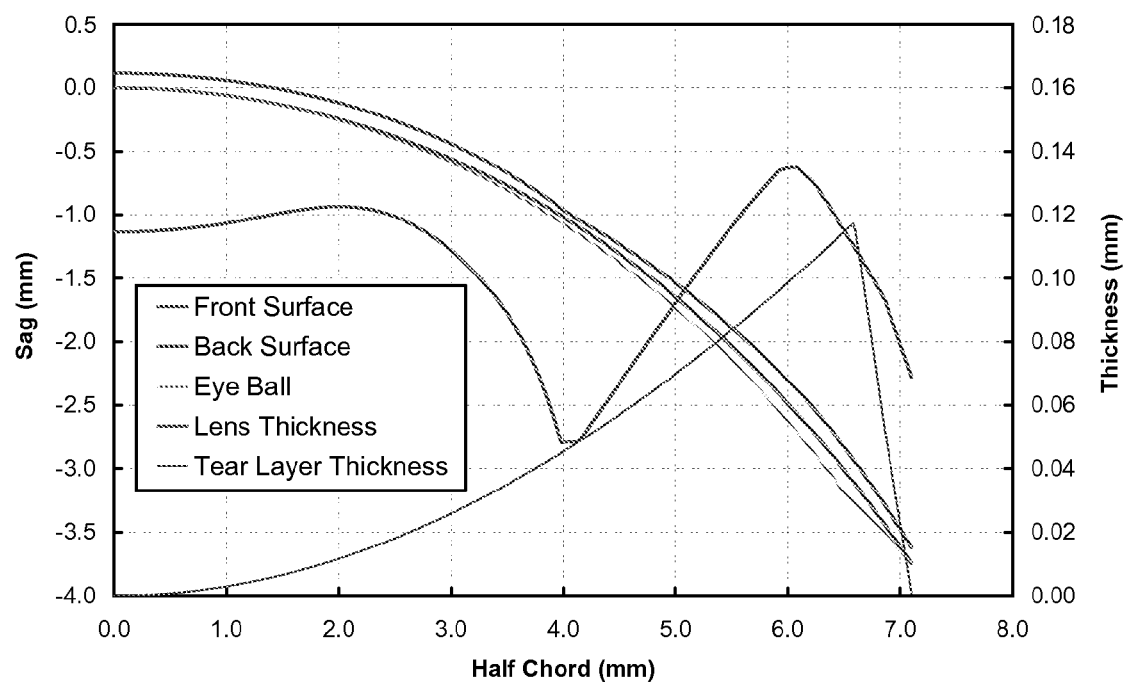
FIG. 7 is the design diagrams of the example contact lens of FIG. 5 showing the thickness profile and surface forms of the example contact lens as well as the surface form of the typical cornea and tear layer thickness.

One possible specific design of this example contact lens is shown in FIG. 7 and may be described using an 8th-order polynomial equation with coefficients of $c_4=8.2\times10^{-4}$, $c_5=-1.8\times10^{-3}$, $c_6=1.4\times10^{-3}$, $c_7=04.0\times10^{-4}$, $c_8=3.9\times10^{-5}$, in addition to a basic conic section with central radius ($r_o$) of 8.782 mm and a conic constant of −0.774 for the front surface and a conic section with central radius ($r_o$) of 8.28 mm and a conic constant of −0.16 for the back surface with a central thickness of 0.12 mm. However, it would be understood by those skilled in lens design that the above and equivalent optical outcomes may be achieved by using other lens design definitions and parameters including but not limited to spherical surfaces, conic sections, splines, Beziers, Fourier synthesis, Zernike polynomials, sagittal height descriptors, radius by angle (R-theta) descriptors and direct look-up tables of surface points, either individually or in various combinations.

The principle as defined by the foregoing method for the design of a vision treatment device for reducing the progression of myopia, but which also incorporates a para-central vision priority zone, is extended in the following sections to demonstrate how this method of design may be used to provide vision priority zones of various configurations on vision treatment devices that employ control of curvature of field to reduce or eliminate the progression of myopia. In later sections, successively more sophisticated approaches to designs of vision treatment devices which, while slightly reducing the expanse of control of curvature of field (i.e. the vision treatment zone) in some regions on the devices, retains a majority of curvature of field control suitable for the reduction or elimination of myopia-inducing stimuli (per U.S. Pat. No. 7,025,460) but in addition, reduces the poor visual performance, especially in the para-central to far periphery, associated with the control of curvature of field, thereby providing the benefit of good vision at certain desired vision priority zones for the wearer. In particular, the methods and devices of this current invention are not only effective in reducing or eliminating the visual impact of other optical aberrations, but also effective in reducing or eliminating the visual impact of peripheral defocus present in decenterable devices as a result of controlling curvature of field.

The influence of peripheral defocus will now be explained. As described above, by controlling curvature of field, or manipulating the position of the peripheral image points to treat myopia, vision treatment devices can incur undesirable other optical aberrations in off-axis directions that can adversely affect vision in those off-axis visual directions. This effect influences both centered vision correction/treatment devices and methods (i.e. those that remain relatively aligned and co-axial with the eye during use such as conventional contact lenses, intra-ocular lenses, corneal in-lays and on-lays, anterior chamber lenses and corneal refractive surgical methods) as well as decenterable vision correction/treatment devices and methods (i.e. those whose position and orientation change according to the direction of gaze of the eye, such as translating contact lenses and spectacle lenses).

In addition, another effect by which controlling curvature of field, or peripheral focal point positions, can influence vision adversely in off-axis visual directions is that of peripheral defocus. This effect influences primarily decenterable vision correction/treatment devices and methods. This effect is illustrated as follows; drawing on the example of a spectacle lens, which is one type of decenterable vision correction device.

The spectacle lens is suited to the control of curvature of field, as it is located some distance from the pupil of the eye. This distance makes the design and control of curvature of field of a spectacle lens simpler and more effective. However, one property of the spectacles lens (a property which is intrinsic to all decenterable vision correction devices) is that it does not remain aligned (i.e. co-axial) with the line-of-sight of the eye during use. As the direction of gaze of the wearer changes (by rotating his eyes to fixate to different parts of his visual world), each eye would be looking through different points (other than the central on-axis point) on the spectacle lens. In other words, the eye looks through different optical points on a spectacle lens depending on its direction of gaze.

When a spectacle wearer is looking straight-ahead and into the distance (the most frequently adopted visual direction), each eye is looking through what may sometimes be called the "distance visual point". Typically, the distance visual point is positioned at the optical center (central, on-axis point) of the spectacle lens. However, when the wearer is reading, both eyes tend to point downwards and converge (i.e. point slightly closer towards the direction of the nose). In this visual direction, each eye is looking through a point positioned relatively lower and more nasally (i.e. towards the nose) than the distance visual point. This point is sometimes called the "near visual point". The amount by which the near visual point is lower or more nasally placed than the distance visual point depends on the anatomical features of the wearer (e.g. the inter-pupillary distance; which is the distance between the centers of the pupil of the two eyes), the reading distance (i.e. the distance from the reading material surface to the eye) and the vertex distance (i.e. the distance from the spectacle lens to the eye) and a number of other parameters that are well known to those skilled in the design and dispensing of spectacle lenses.

At other times, for example when driving, the wearer may need to scan along a horizontal line (e.g. to check for traffic in the cross street at a junction). In this case, each eye may be looking at any of a number of points lying in a horizontal line, which may pass through the distance visual point of the spectacle lens.

The commonality of the above scenarios is that when the visual object of interest to the wearer is in a direction other than straight-ahead, the wearer's eye is directed to view through a point or region of the spectacle lens which is not the central on-axis point of the spectacle lens. If a particular direction of gaze is frequently required by the wearer and the vision in that direction of gaze needs to be good (e.g. in the case of the near visual point, the wearer may be a clerical worker frequently needing to read), the region(s) on the lens associated with the critical direction(s) of gaze may be considered to be a vision priority zone of the wearer.

When a lens is designed to control the curvature of field (i.e. control the positions of the peripheral image points) for reducing myopia progression, that lens is relatively more positive in refractive power at points (i.e. corresponding to different visual directions of gaze) away from its optical center. While this effect occurs in a three-dimensional manner—i.e. proceeding away from the optical center along any chosen meridian on the lens, the concept may be adequately illustrated by consideration in two-dimensions as shown in FIGS. 8A through 8C.

Figure 8A:
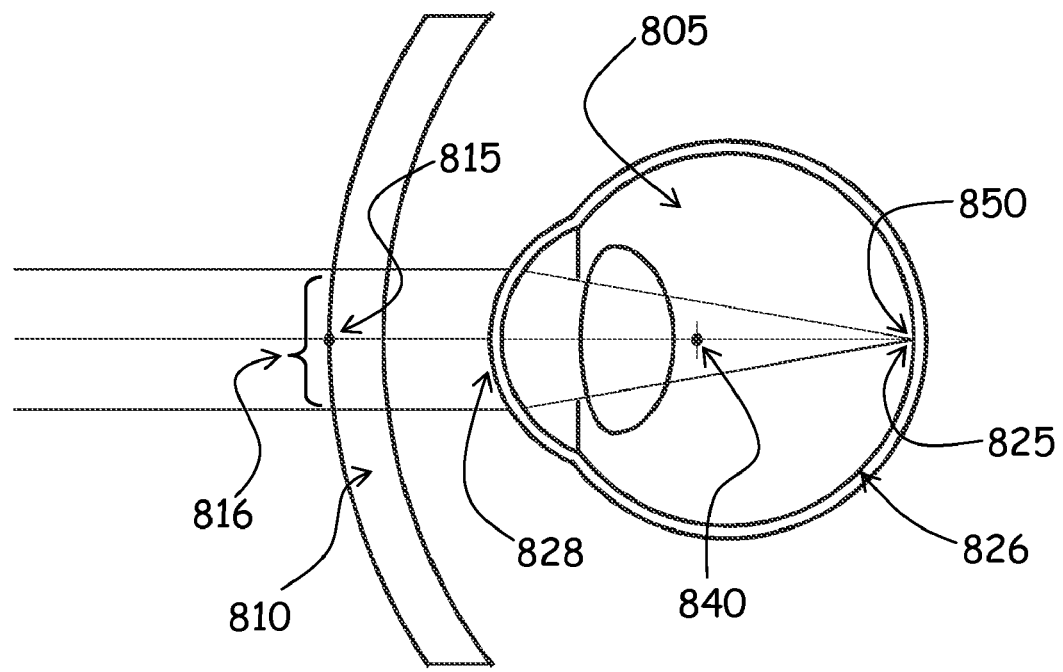
FIGS. 8a-c explain the origin of peripheral defocus for a decenterable vision correction device.
Figure 8B:
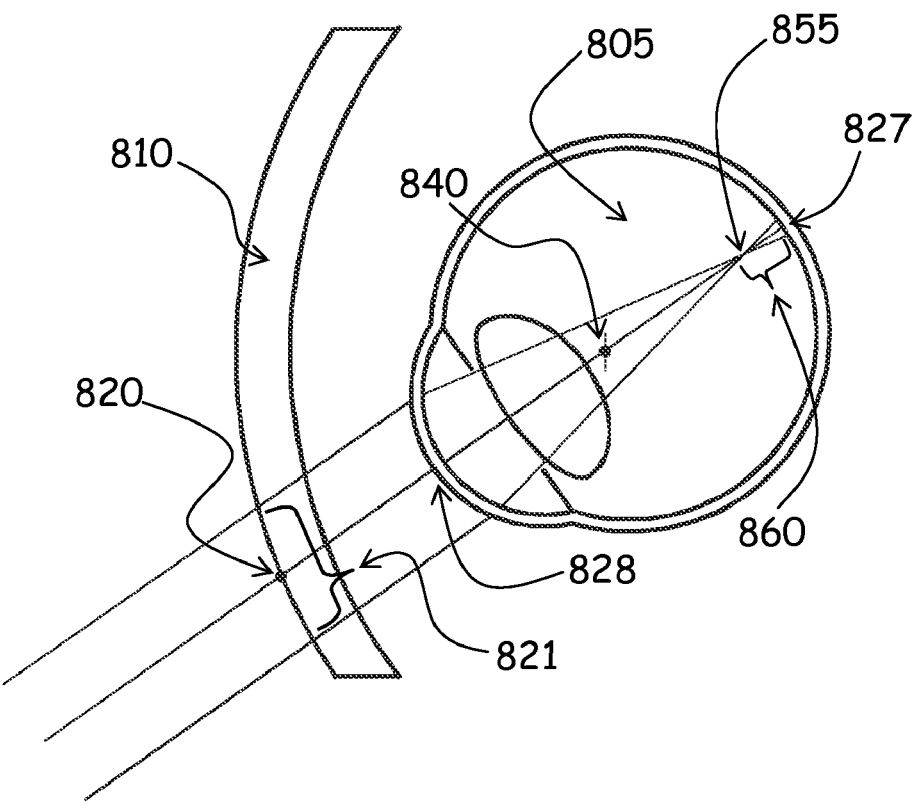
Figure 8C:
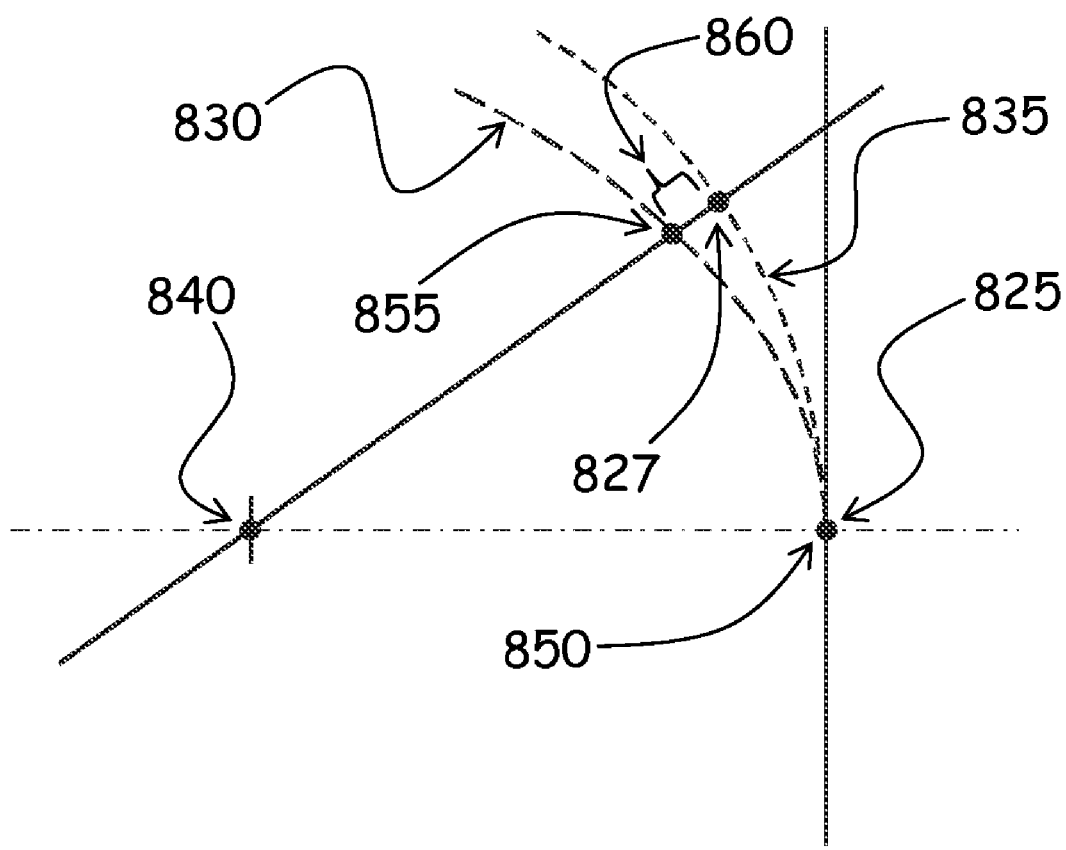

In FIG. 8A, an eye 805 looking in the straight-ahead gaze is fitted with a spectacle lens 810. In this direction of gaze, the eye 805 is looking through the optical center 815 and its surrounding region 816, which is also the distance visual point of the spectacle lens 810. In FIG. 8B, the same eye 805 fitted with the same spectacle lens 810 is now in a downward gaze (e.g. for reading). In this direction of gaze, the eye 805 is now looking through a more peripheral optical point 820 and its surrounding region 821 on the spectacle lens 810.

Since, in this case, the spectacle lens 810 has been designed to incorporate control of curvature of field, its power in the straight-ahead direction (through the optical center 815) is manipulated to place the focal point 850 on to the fovea 825 on the retina 826 of the eye 805 thereby providing good central, on-axis vision while simultaneously, its power in the periphery (e.g. through peripheral optical point 820) would, progressing away from the optical center 815, become increasingly positive relative to the power at the optical center. This is shown as a curvature of field plot in FIG. 8C. In FIG. 8C, a curve representing the relative curvature of field 830 of spectacle lens 810 is shown. FIG. 8C also shows the "foveal sphere" 835 of the fovea 825 of the eye 805 as it rotates from straight-ahead gaze to a downward gaze. This sphere describes the locus of all locations that the fovea (in FIGS. 8A through 8C, 825 for straight-ahead, and 827 for peripheral/downward gaze) may adopt as the eye 805 rotates downwards. This foveal sphere 835 is centered about the center of rotation 840 of the eye, which although is not a fixed point physiologically and varies from eye to eye, is usually considered to lie approximately on the axis of the eye and is approximately 16 mm behind the cornea 828 of the eye. Since the spectacle lens 810 has been designed to control curvature of field for the reduction of myopia progression, its power becomes more positive away from the axial position as illustrated by the curvature of field plot 830 of FIG. 8C. The focus 850 is placed on the fovea in straight-ahead gaze so that clear central vision is provided. However, on peripheral gaze, the peripheral focal point 855 is positioned relatively in front of (i.e. closer towards the cornea from the retina) the fovea 827 due to the more positive refractive power. This difference in position of the fovea 827 during peripheral gaze and its corresponding focal point position 855 introduces an amount of defocus 860 causing blurred foveal vision on peripheral gaze.

It should be noted that, depending on the exact design and position of the spectacle lens relative to the eye, the amount of curvature of field control employed for reduction of myopia progression, as well as the anatomical dimensions of the eye (some of which has been described above), the peripheral defocus may either be in front of (as in this example) or behind the fovea.

In practice, for decenterable vision devices, both peripheral defocus and other optical aberrations (as explained in earlier sections) are present substantially simultaneously for peripheral directions of gaze. These two effects combine and summate to degrade the visual image quality for peripheral directions of gaze. Both of these effects increase from the central optical center, through the para-central region to the far periphery.

In the general usage of decenterable vision devices, peripheral defocus combined with other optical aberrations may not be a concern as the most frequent direction of gaze of wearers is typically either straight-ahead (central) or nearly straight-ahead (para-central) for which the defocus is nil to very low. However, for certain wearers, those engaging in visual tasks that require prolonged periods of viewing through peripheral optical points, especially points that may be considered to be vision priority regions, this defocus would be undesirable.

It may be necessary in some instances to provide for useful, relatively good vision beyond the para-central region. For example, a wearer may need to have relatively good useful peripheral vision along a horizontal line (e.g. during driving, making use of his peripheral vision to detect vehicles entering from a cross-street at a traffic junction). In such a situation, the vision priority zone required by the wearer may be an optical region described by a band lying in a horizontal line.

It should be noted that good vision as relating to peripheral vision is a relative measure since it is known that the density of photoreceptors is in the highest concentration at the central (foveal) region, providing the best visual acuity, and decreases towards the periphery of the retina. Thus, visual acuity in the periphery is not as good as acuity for foveal vision. However, if the magnitude of other optical aberrations and defocus is sufficiently great, vision and in particular, contrast sensitivity (a measure of how well the eye can discern between subtle grades of black through gray to white as known to experts in vision science), may suffer. Hence, improvements in peripheral vision can be made by reducing the severity of other optical aberrations present.

In another example already mentioned, a wearer may need to engage in long durations of reading at a fixed distance during which both eyes are converged and may also be in a downward gaze. In such a situation, the vision priority zone required by the wearer may be described by an optical region of the vision treatment device which includes and encloses the near visual point of the device.

In yet another example, a wearer (e.g. and assembly line inspector) may need to frequently visually scan from distance visual objects to near visual objects. In such a situation, the vision priority zone required by the wearer may be a region described by a band joining and including and enclosing the distance visual point and the near visual point on the device.

We will now illustrate by example, successively more sophisticated approaches to designs of vision treatment devices which addresses the needs of the wearers as described above by the incorporation of appropriate vision priority zones to a vision treatment device that employs a vision treatment zone used to control curvature of field in order to reduce the progression of myopia. The common theme is the control, reduction or minimization of other optical aberrations and/or peripheral defocus within the vision priority zone so that vision through the vision priority zone is improved and becomes useful for the wearer. The reduction or elimination of other optical aberrations and/or peripheral defocus is achieved by the localized moderation or removal of curvature of field control in the select vision priority zones.

As will be illustrated in the examples to follow, only a minority of reduction to the expanse of curvature of field control will be incurred as a consequence of controlling or reducing other optical aberrations and/or defocus at certain vision priority zones. Thus, while the overall total curvature of field control may be slightly reduced, and hence the overall myopia-reducing stimuli may be slightly reduced (but not eliminated), the benefit of clear vision at the desired visual points (e.g. for reading) would provide a comparatively better and more advantageous outcome (in terms of both myopia-reduction and usefulness and clarity of vision) for the wearer.

Figure 9A:
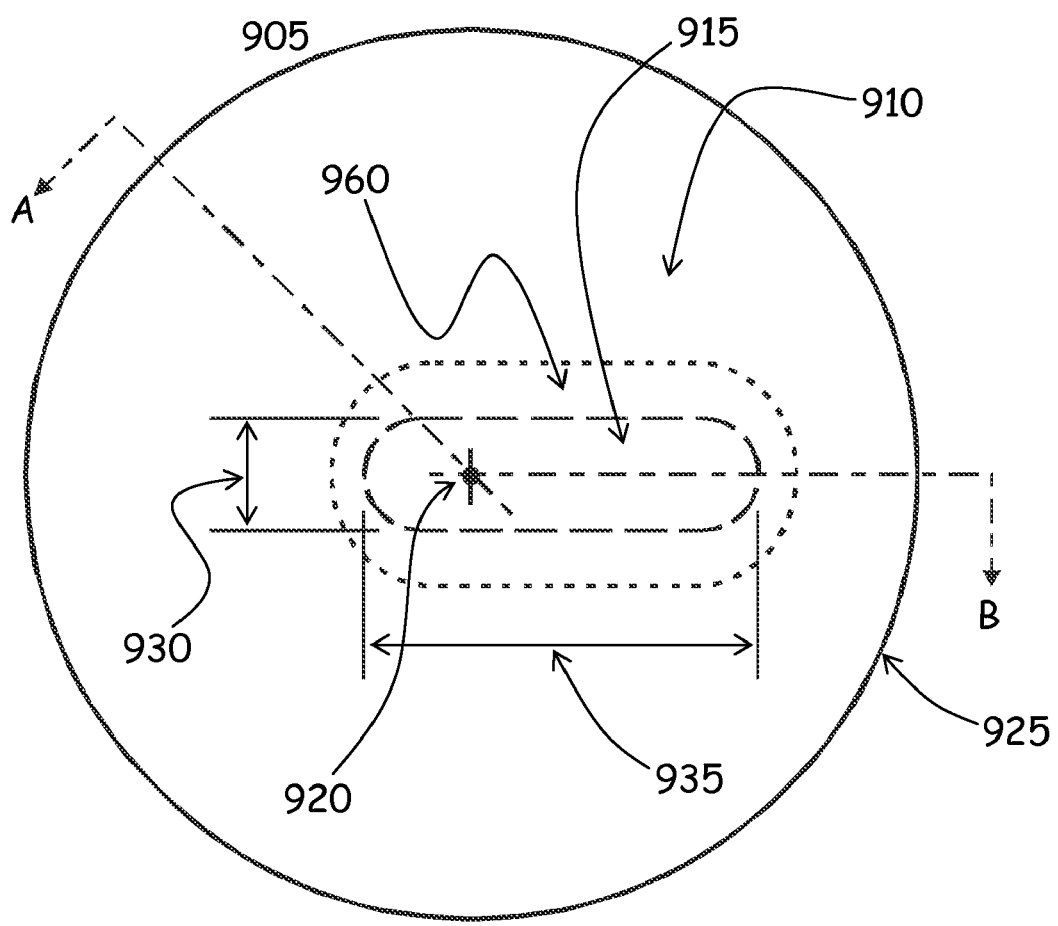
FIGS. 9A-C are design examples of one embodiment of the present invention.
Figure 9B:
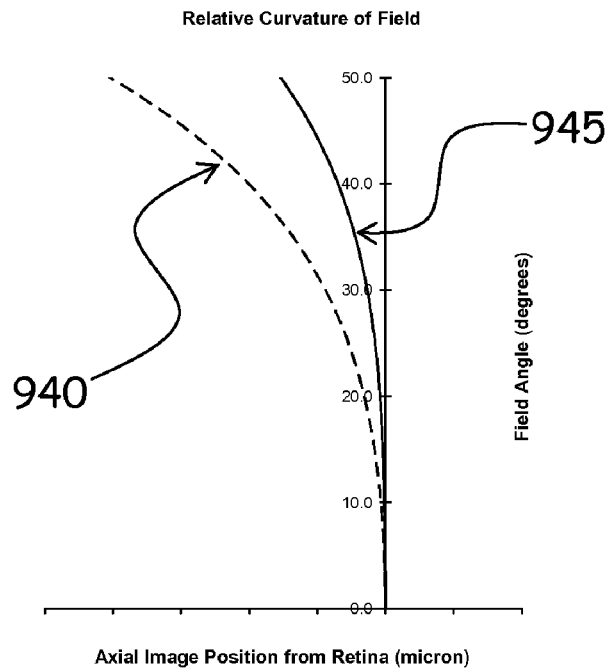
Figure 9C:
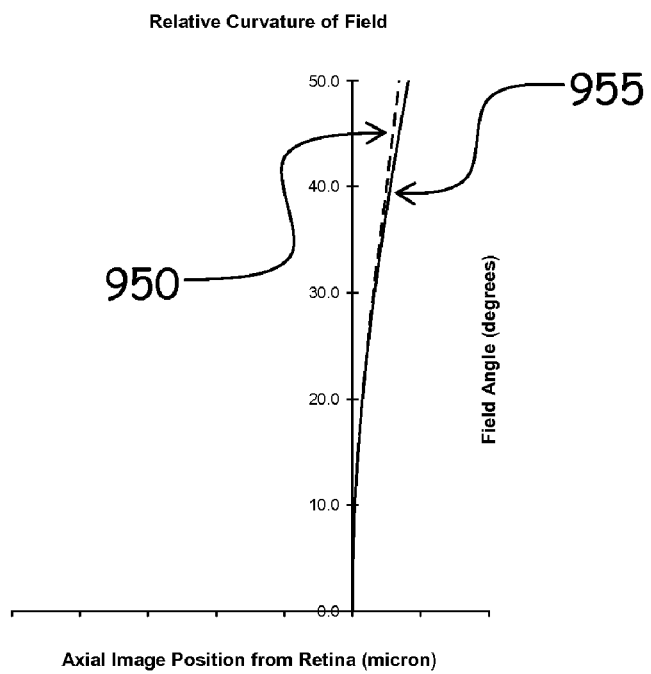

For the wearer who needs to have relatively good, useful peripheral vision along a horizontal line of directions of gaze (e.g. during driving), a method of design of the current invention is shown in FIGS. 9A through 9C. FIG. 9A is a front-on view of the optical configuration of the vision treatment device of this method. FIGS. 9B and 9C are relative curvature of field plots. On to a vision treatment device 905 that consists chiefly of a vision treatment zone 910 that provides the appropriate relative curvature of field for the purpose of reducing or eliminating myopia progression as taught by U.S. Pat. No. 7,025,460, the method of the current invention introduces and incorporates a band of vision priority zone 915. The vision priority zone 915 of this design method is described by a band that includes the optical center 920 of the device and continues in either/both directions partially or totally to the boundary 925 of the optics of the vision treatment device. The width 930 of the band of this vision priority zone 915 will be at least approximately the size of the projection of the entrance pupil of the wearer on to the device along the same rationale as explained in a previous section.

According to a method of this invention, within the vision priority zone 915, the impact of other optical aberrations is controlled, reduced or minimized by moderating or removing the control for curvature of field. Instead of controlling for curvature of field (or manipulating the positions of the peripheral image points), the optical design degrees of freedom for the device within the vision priority zone is employed to optimize on one or other of the other optical aberrations and/or defocus according to their severity and the visual needs of the wearers. FIG. 9B shows the relative curvature of field as measured along a meridian "A" within the vision treatment zone 910 of the vision treatment device 905 of FIG. 9A. It is clear from the plot of FIG. 9B that the vision treatment zone 910 is providing the curvature of field control useful for the retardation or elimination of myopia progression as taught by U.S. Pat. No. 7,025,460. It can also be seen from FIG. 9B that the vision treatment zone 910 suffers from amounts of other optical aberrations including astigmatism. The tangential 940 and sagittal 945 line foci of FIG. 9B are separated indicating the presence of substantial amounts of astigmatism. Hence, peripheral vision within the vision treatment zone 910 will be poor. In contrast, FIG. 9C shows the relative curvature of field as measured along a meridian "B" along the band of the vision priority zone 915 for the same vision treatment device 905 of FIG. 9A. In this particular example design, one of the other optical aberrations, namely astigmatism, has been minimized in order to provide improved vision along the vision priority zone for the wearer. This can be seen clearly in FIG. 9C in that both the tangential 950 and sagittal 955 line foci of astigmatism are in close proximity to each other indicating the lack of astigmatism along the vision priority zone.

It can be seen that both line foci 950 and 955 of astigmatism lie behind the retina along this meridian B indicating a relative hyperopic (i.e. relative negative power) defocus. This small amount of negative defocus can be readily compensated for by a small amount of accommodation (i.e. near focusing) on the part of the wearer.

The method of design would now yield a vision treatment device which provides the dual benefit of reduction of myopia progression as well as good, useful vision along directions of gaze important to the wearer. Since the area of the vision priority zone 915 is small compared to the vast area of the vision treatment zone 910, there is only a slight, insignificant reduction in the delivery of stimulus to reduce myopia progression in the design approach of this invention.

As one skilled in lens design would appreciate, in light of the teachings of the present invention per foregoing, the optical 'junction' zone 960 bordering between the vision treatment zone 910 and the vision priority zone 915 would need to be modified slightly in curvature of field control in order to provide a smooth optical transition (e.g. free of visual 'jump') from the controlled curvature of field vision treatment zone 910 to the vision priority zone 915.

The length 935 of the vision priority zone 915 may be chosen according to the visual needs of the wearers. For example, a length that provides for a band that extends the optics of the vision treatment device from boundary to boundary may be of benefit to a wearer whose primary visual need is for driving. Such a band has the added benefit of being simpler to manufacture as it exhibits mirror (lateral) symmetry. For wearers who prefer to maximize the expanse of the vision treatment zone to maximize the stimulus for reduction of myopia progression, shorter vision priority zone band lengths (providing only for the critical directions of gaze) may be chosen. The band may be asymmetrically disposed such that one end of the band is further from the optical center 920 than the other end. This may be useful for wearers whose most frequent visual task requires convergence of the two eyes (i.e. each eye turning inwards towards the nose) as, for example, when the reading material is at eye-level (e.g. shelf-mounted laboratory/medical monitoring equipment).

Figure 10:
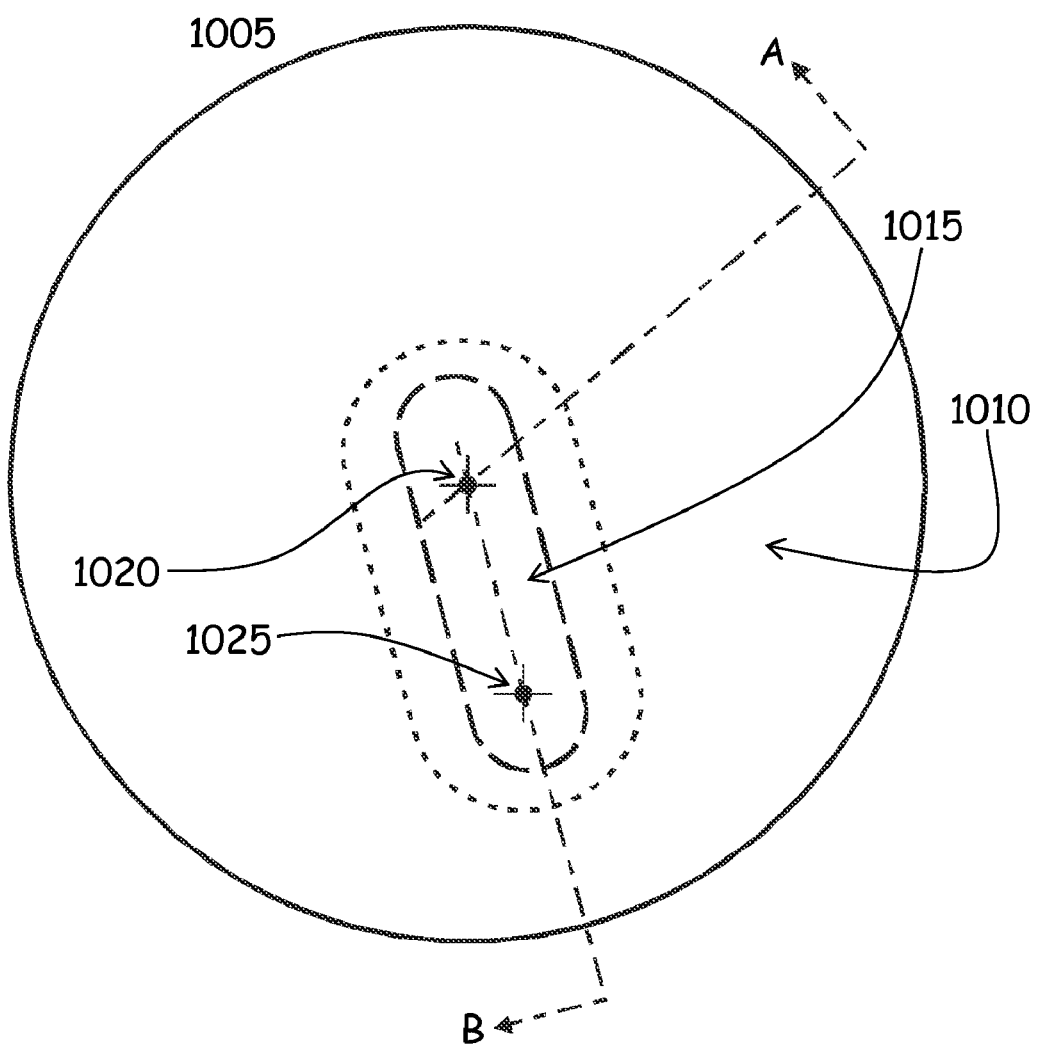
FIG. 10 is another design example of an embodiment of the present invention showing the front-on design layout of the vision treatment device having a vision priority zone band that includes the distance and near visual points of the vision treatment device.

It would also be immediately clear given the foregoing that the band of the vision priority zone of the example in FIG. 9A need not be horizontally disposed. FIG. 10 provides an example of when the band of the vision priority zone 1015 is configured to lie on an oblique meridian of the vision treatment device 1005. In this example, the vision priority zone 1015 band includes the optical center 1020 (which is also the distance visual point of the vision treatment device 1005) as well as the near visual point 1025. Such a design would be of benefit to a wearer (e.g. and assembly line inspector) who may need to frequently visually scan from distance visual objects to near visual objects. This design would maintain the visual points of the eye, as its direction of gaze traverses from distance to near via the intermediate viewing distance (involving convergence and downward gaze of the eyes), within the vision priority zone 1015. It would be appreciated that, for this example wearer, the layout of the vision priority zone(s) of this vision treatment device would be approximately mirror symmetrical for the right and left eye. FIG. 10 shows the front-on view (as seen looking towards the wearer's face) of a vision treatment device for the right eye of the wearer.

Those skilled in the design and dispensing of ophthalmic vision correction devices would appreciate, and the present invention therefore contemplates, that such a device would require correct positioning and orientation on the eyes. For vision treatment device in the form of spectacle lenses, correct mounting is provided by the spectacle frame which sets the correct orientation of the lens device. For contact lenses and other similar devices, design features suitable for correct orientation of the device are well known to practitioners of ophthalmic vision correction devices and include prism ballasting, dynamic thin zones, and 'slab-off' designs. Fabrication of such asymmetrical design devices is also well known to those skilled in the art and includes the use of computer-controlled multi-axis lathes and mills. In the case of implantable devices such as corneal in-lays and on-lays, anterior chamber lenses and intra-ocular lenses, and refractive surgical methods, alignment devices to assist in their correct orientation during implantation (e.g. visible alignment marks, fenestrations for facilitating alignment with special implements, etc.) or surgery (e.g. laser-assisted eye-tracking systems) and design fixtures for maintaining orientation in the devices (e.g. spring-loaded haptics in intra-ocular lenses) are all well-known to designers and practitioners using such devices.

The relative curvature of field for this design example along meridians "A" within the vision treatment zone 1010 and along meridian "B" within the vision priority zone 1015 may be similar to those shown in FIGS. 9b and 9c respectively. As for previous design examples given above, the width of the vision priority zone 1015 would be at least approximately the size of the entrance pupil of the eye projected onto the optical surface of the vision treatment device but may be larger and selected according to the visual needs of the wearer.

One potential drawback of the above examples for which the vision priority zone is configured as a band across the optical surface of the vision treatment device is it may reduce the overall area of the vision treatment zone more than is absolutely necessary. In addition, as understood by those skilled in lens design, the optical design of a band may introduce undesirable optical aberrations at the optical junction zone. For the wearer who requires a vision priority zone for principally a single direction of gaze in addition to the straight-ahead gaze, this potential drawback can be minimized by limiting the vision priority zone to provide only for that select direction of gaze. For example, for the wearer whose main visual needs is for reading, with the direction of gaze through the near visual point of the vision treatment device, a method of the invention is to configure the vision priority zone to be located only on and around the near visual point. In doing so, greater amount of overall curvature of field control is retained than for the previous design examples utilizing band configurations for the vision priority zone (albeit with greater involvement in lens design and manufacturing complexity).

Figure 11A:
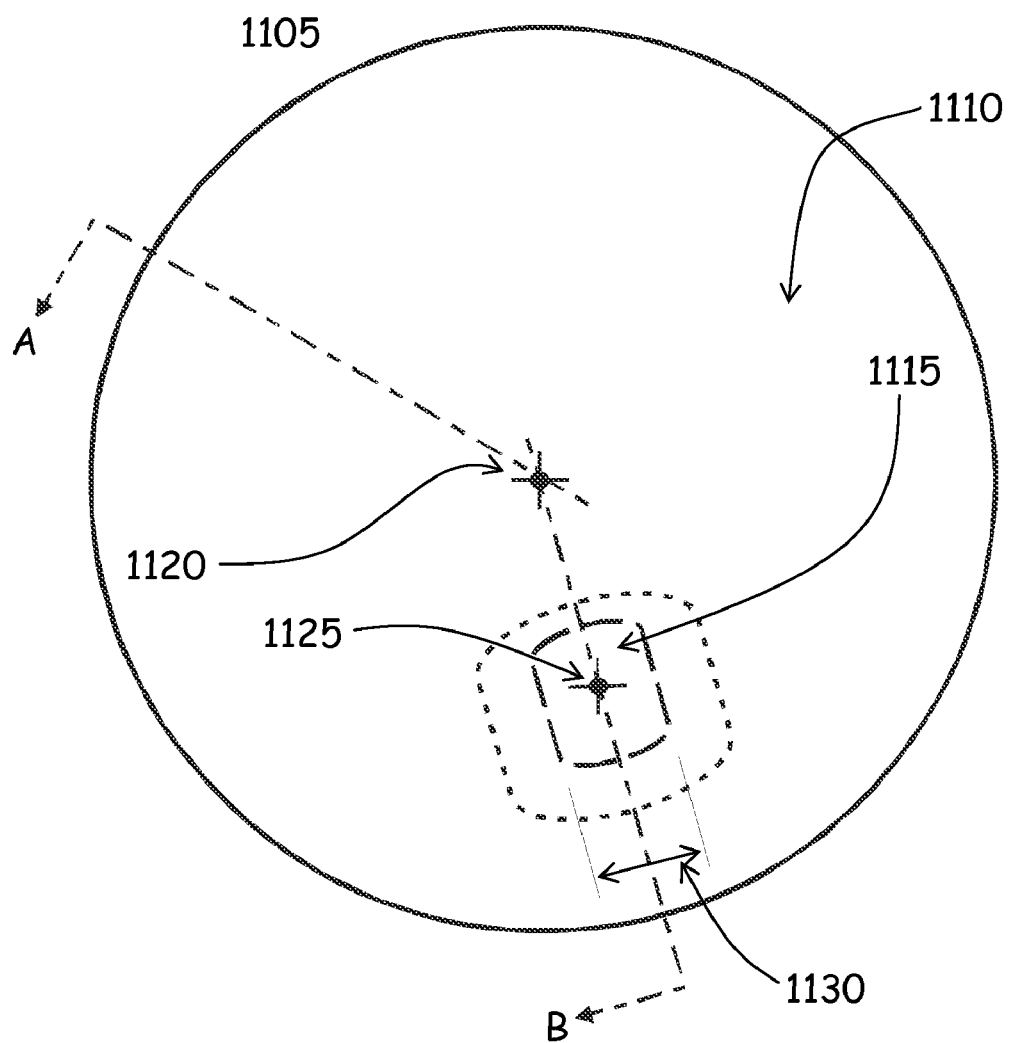
FIGS. 11A-C show another design example of one embodiment of the present invention.
Figure 11B:
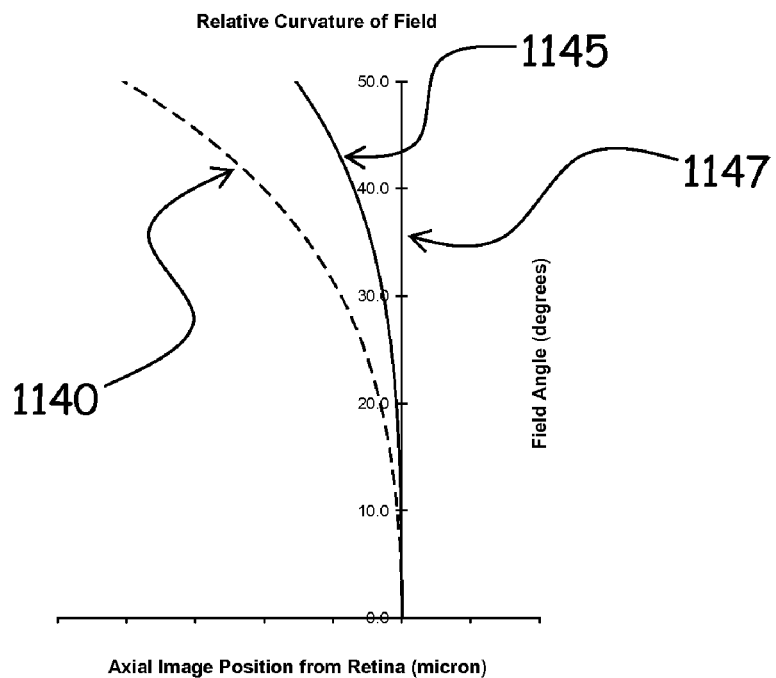
Figure 11C:
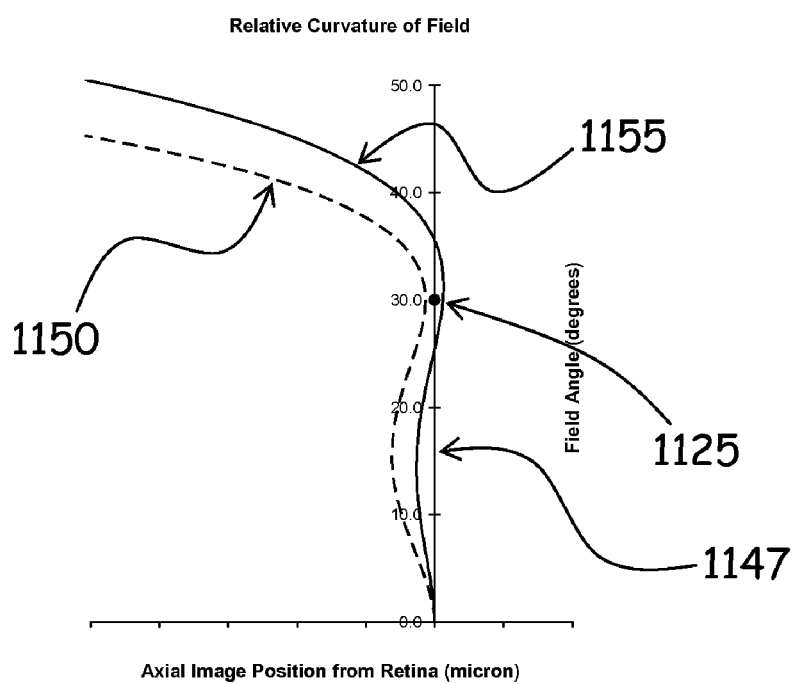

FIGS. 11A through 11C illustrate a vision treatment device 1105 applicable for this example. In FIG. 11A, the front-on view of the optical surface of a vision treatment device 1105 intended for the right eye of the wearer is shown. The vision treatment device 1105 consists chiefly of a vision treatment zone 1110 that provides the appropriate relative curvature of field for the purpose of reducing or eliminating myopia progression as taught by U.S. Pat. No. 7,025,460. The method of the current invention introduces and incorporates a region of vision priority zone 1115 that includes the near visual point 1125. While the vision priority zone 1115 region may be of any shape (e.g. circular, elliptical, rectangular, etc), the minimum dimension 1130 of this vision priority zone 1115 will be at least approximately the size of the projection of the entrance pupil of the wearer on to the device along the same rationale as explained in a previous section.

According to a method of this invention, within the vision priority zone 1115, the impact of other optical aberrations is controlled, reduced or minimized by moderating or removing the control for curvature of field. Instead of controlling for curvature of field (or manipulating the positions of the peripheral image points), the optical design degrees of freedom for the device within the vision priority zone is utilized to optimize on peripheral defocus or one or other of the other optical aberrations according to their severity and the visual needs of the wearers. FIG. 11B shows the relative curvature of field as measured along a meridian "A" within the vision treatment zone 1110 of the vision treatment device 1105 of FIG. 11A. It is clear from the plot of FIG. 11B that the vision treatment zone 1110 is providing the curvature of field control useful for the retardation or elimination of myopia progression as taught by U.S. Pat. No. 7,025,460. It can be seen from FIG. 11B that the vision treatment zone 1110 suffers not only from amounts of other optical aberrations including astigmatism but also peripheral defocus. The tangential 1140 and sagittal 1145 line foci of FIG. 9B are separated indicating the presence of substantial amounts of astigmatism. But in addition, both the tangential 1140 and sagittal 1145 line foci are positioned more anteriorly to the retina 1147 indicating an amount of peripheral defocus is present. Unlike negative (hyperopic) defocus, positive (myopic) defocus cannot be compensated for by accommodation. Hence, peripheral vision within the vision treatment zone 1110 will be poor. In contrast, FIG. 11C shows the relative curvature of field as measured along a meridian "B" along the vision priority zone 1115 region for the same vision treatment device 1105 of FIG. 11A. In this particular example design, peripheral defocus through the near visual point 1125 has been minimized in order to provide improved vision within the vision priority zone for the wearer. This can be seen clearly in FIG. 11C in that while there remains some distance between the tangential 1150 and sagittal 1155 line foci at the near visual point 1125 indicating the presence of a small amount of astigmatism, both of these line foci are approximately equally disposed about (i.e. one in front of and the other behind) the retina 1147 indicating that peripheral defocus at the near visual point 1125 has been significantly reduce and effectively neutralized.

Notice also from FIG. 11C that on either side of the near visual point 1125, both line foci 1150 and 1155 of astigmatism are again positioned to be more anterior than the retina 1147 producing stimulus to reduce the progression of myopia.

The method of design would now yield a vision treatment device which provides the dual benefit of reduction of myopia progression as well as good, useful vision along directions of gaze important to the wearer. Further, this design example offers less compromise and intrusion to the vision treatment zone 1110, thereby maximizing the delivery of stimulus to reduce myopia progression.

In foregoing examples, the design of the vision priority zone has been optimized to minimize one of the other optical aberrations (e.g. astigmatism) or peripheral defocus. It is also possible, within the method of the current invention, to utilize the degree of freedom in design made available through the localized moderation or removal or control for curvature of field to manipulate other optical design parameters. For example, instead of minimizing or removing peripheral defocus, defocus through the vision priority zone may be designed and controlled to be of a particular value.

It has been noted in the scientific literature that myopia progression may be reduced by employing the under-correction method. It is also stated in scientific publications that myopia progression may be associated with accommodation during near viewing. Accommodation is the process by which the eye changes (increase) its optical power during reading in order to provide clear focus for near visual objects. While the disadvantages associated with under-correction has already been discussed in earlier sections, it may be of benefit to reduce the demand on accommodation during near work as an added stimulus to reducing the progression of myopia. Therefore, it may be advantageous for applications in which the vision priority zone includes the near visual point to incorporate an amount of positive power to the vision priority zone. In this way, the benefit of reducing or eliminating the stimulus to myopia progression may be further enhanced by the reduction in accommodative demand during near viewing.

Figure 12A:
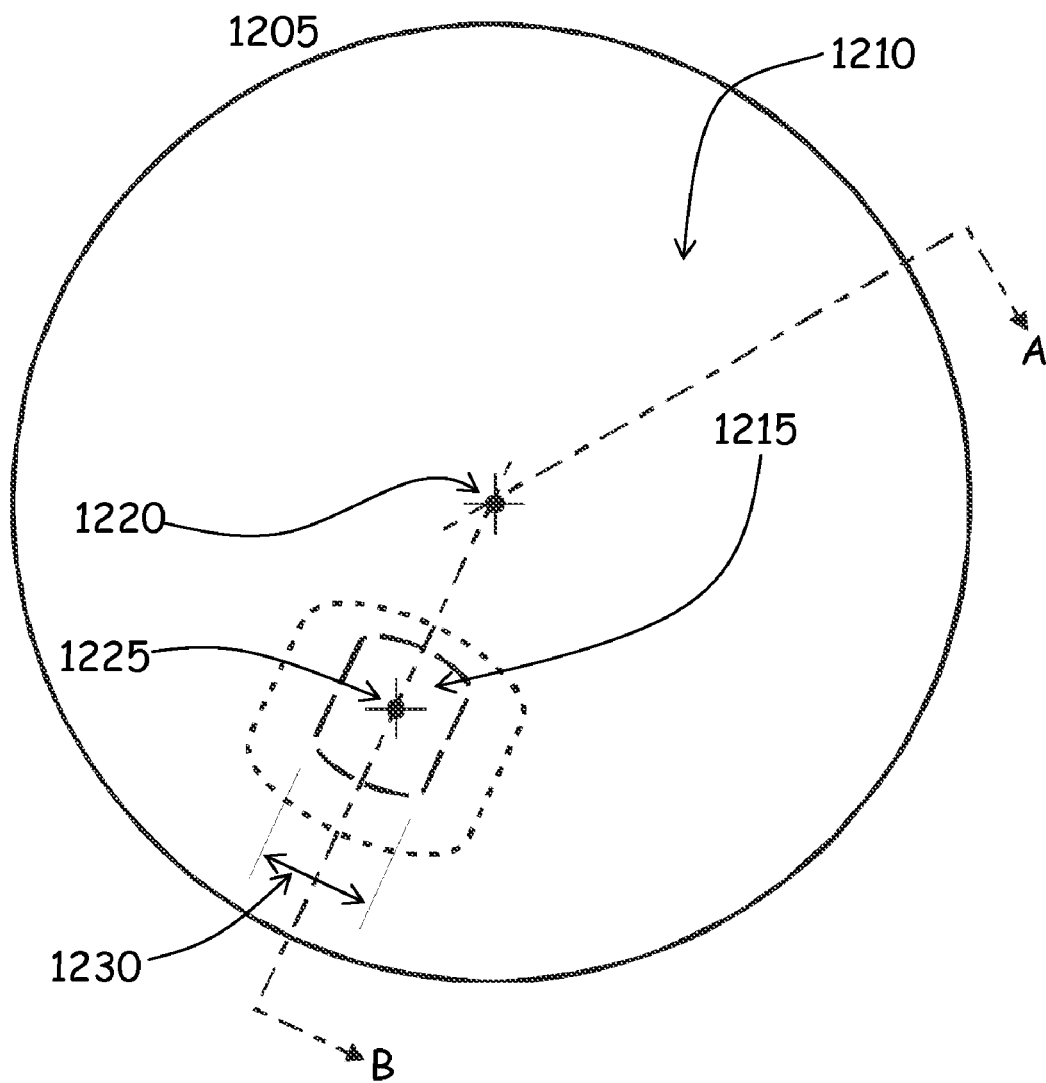
FIGS. 12A-C show another design example of one embodiment of the present invention.
Figure 12B:
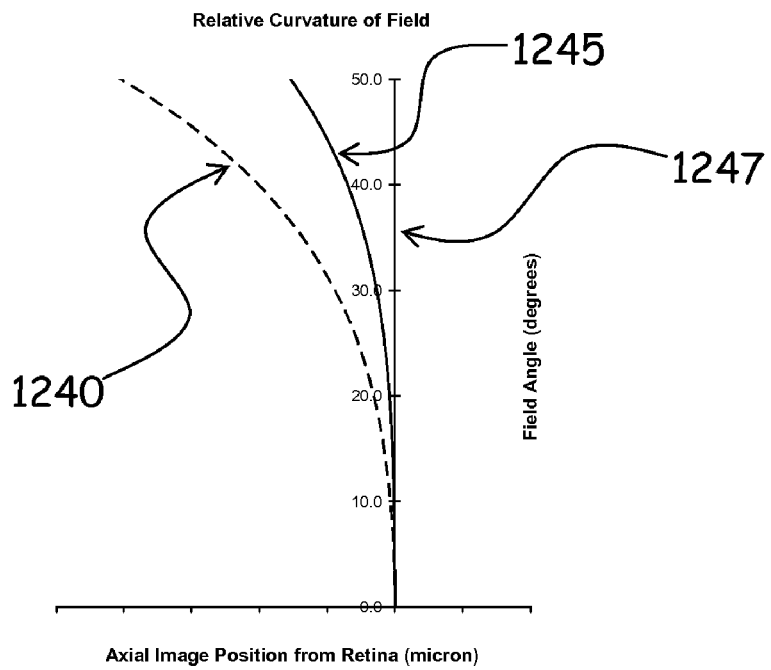
Figure 12C:
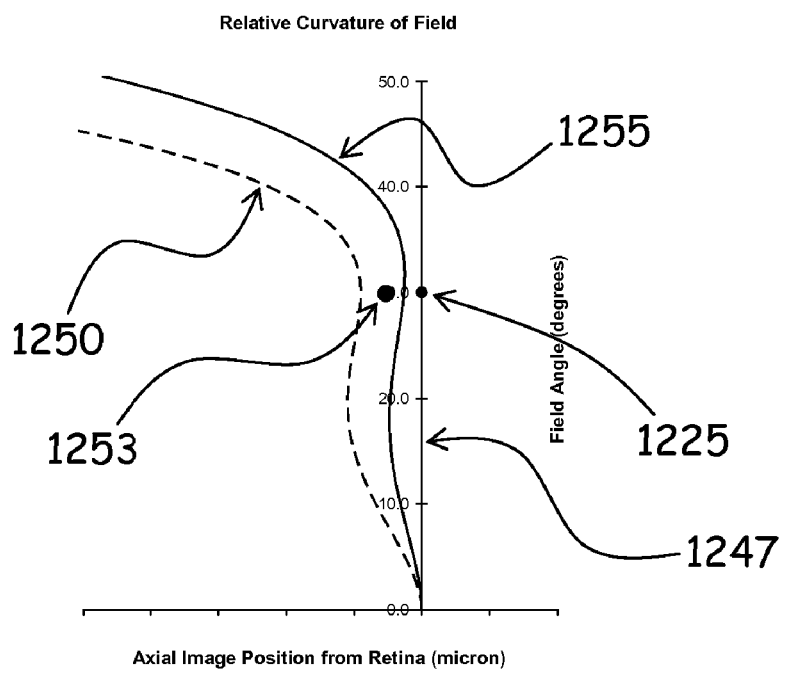

An example for such an application is shown in FIGS. 12A through 12C in which additional positive power (to introduce myopic defocus) is introduced into a vision priority zone which includes the near visual point.

In FIG. 12a, the front-on view of the optical surface of a vision treatment device 1205 intended for the left eye of the wearer is shown. The vision treatment device 1205 consists chiefly of a vision treatment zone 1210 that provides the appropriate relative curvature of field for the purpose of reducing or eliminating myopia progression as taught by U.S. Pat. No. 7,025,460. The method of the current invention introduces and incorporates a region of vision priority zone 1215 that includes the near visual point 1225. While the vision priority zone 1215 region may be of any shape, the minimum dimension 1230 of this vision priority zone 1215 will be at least approximately the size of the projection of the entrance pupil of the wearer on to the device.

According to a method of this invention, within the vision priority zone 1215, peripheral defocus is controlled to deliver a relatively positive power (defocus) up to about +4.50 D. FIG. 12B shows the relative curvature of field as measured along a meridian "A" within the vision treatment zone 1210 of the vision treatment device 1205 of FIG. 12A. It is clear from the plot of FIG. 12B that the vision treatment zone 1210 is providing the curvature of field control useful for the retardation or elimination of myopia progression as taught by U.S. Pat. No. 7,025,460. FIG. 12C shows the relative curvature of field as measured along a meridian "B" along the vision priority zone 1215 region for the same vision treatment device 1205 of FIG. 12A. In this particular example design, peripheral defocus through the near visual point 1225 has been controlled to be relatively positive of up to +4.50D. This can be seen in FIG. 12C in that in the region of the near visual point 1225 within the vision priority zone 1215, the equivalent 'best focus' 1253 (also called the "circle of least confusion" which is defined by the dioptric average between the tangential 1250 and sagittal 1255 line foci of astigmatism) lies more anteriorly than the retina 1247 providing greater amounts of positive power at near. This additional near power reduces the demand on accommodation on the part of the wearer during near work.

The method of design would now yield a vision treatment device which provides the dual benefit of reduction of myopia progression as well as good, useful vision along directions of gaze important to the wearer. Further, this design example offers the additional benefit of reducing the accommodative demand during near work which may reduce the stimulus on progression of myopia.

In the foregoing examples, specific surface definition techniques (e.g. conics sections and polynomials) have been used to demonstrate how the design methods of the current invention may be achieved. However, it would be understood by those skilled in lens design that equivalent optical outcomes may be achieved by using other lens design definitions and parameters including but not limited to spherical surfaces, conic sections, splines, Beziers, Fourier synthesis, Zernike polynomials, sagittal height descriptors, radius by angle (R-θ) descriptors and direct look-up tables of surface points, either individually or in various combinations.

With the potential introduction of active optical devices with the potential to correct refractive error and ocular aberrations in real-time (e.g. wave-front correction systems and 'adaptive optics' systems), it is contemplated that the design approaches of this invention may also be incorporated in those devices. In addition, the control for certain other optical aberrations and the control of peripheral focus have been used.

Many modifications, variations, and other embodiments of the invention will come to the mind of one skilled in the art to which this invention pertains having the benefit of the teachings presented in the foregoing descriptions. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

We claim:

1. A method for reducing progression of refractive error comprising the steps of:
   providing an optical vision treatment device comprising a vision treatment zone and at least one vision priority zone;
   wherein said vision treatment zone is configured with a predetermined first optical design,
   said first optical design selected to effect control of forward-backward positions of peripheral off-axis focal points relative to a retina;
   said control of positions of peripheral off-axis focal points producing at least one substantially corrective stimulus for influencing progression of refractive error while substantially simultaneously controlling the forward-backward position of a central on-axis focal point near to near the retina and substantially simultaneously providing clear on-axis images; and
   wherein said vision priority zone is configured with a predetermined second optical design;
   said second optical design selected to control, for at least one direction of gaze a condition selected from the group consisting of: peripheral defocus and other optical aberrations.

2. The method according to claim 1, wherein the step of controlling the forward-backward positions of peripheral off-axis focal points, for a vision treatment device that in combination with an eye exhibits astigmatism, further comprises the step of:
   controlling the forward-backward positions of peripheral line foci produced by astigmatism relative to the retina.

3. The method according to claim 2, wherein the step of controlling the forward-backward positions of peripheral line foci further comprises the step of:
   positioning a first peripheral line focus that is nearer to the cornea of the eye than a second peripheral line focus, to a distance from the cornea of the eye towards the peripheral retina, said distance being approximately less than or equal to the distance from the cornea to the peripheral retina.

4. The method according to claim 3, wherein at least one of said vision priority zone is configured to include a region of said vision treatment device, said region selected from the group consisting of: the optical center; the distance visual point; the near visual point; and combinations thereof.

5. The method according to claim 3, wherein at least one of said vision priority zone is configured to include the distance visual point and the near visual point on said vision treatment device.

6. The method according to claim 2, wherein the step of controlling the forward-backward positions of peripheral line foci further comprises:
   positioning a first peripheral line focus that is further from the cornea of the eye than a second peripheral line focus, to a distance from the cornea of the eye towards the peripheral retina, said distance being approximately greater than or equal to the distance from the cornea to the peripheral retina.

7. The method according to claim 6, wherein at least one of said vision priority zone is configured to include a region of said vision treatment device, said region selected from the group consisting of: the optical center; the distance visual point; the near visual point; and combinations thereof.

8. The method according to claim 6, wherein at least one of said vision priority zone is configured to include the distance visual point and the near visual point on said vision treatment device.

9. The method according to claim 4, wherein a minimum width of said vision priority zone is approximately equal to or greater than the size of the entrance pupil of said eye.

10. The method according to claim 7, wherein a minimum width of said vision priority zone is approximately equal to or greater than the size of the entrance pupil of said eye.

11. An optical device comprising:
    a vision treatment zone and at least one vision priority zone;
    wherein said vision treatment zone is configured with a predetermined first optical design;
    said first optical design selected to effect control of forward-backward positions of peripheral off-axis focal points relative to the retina of an eye while substantially simultaneously controlling the forward-backward position of a central on-axis focal point near to near the retina; and
    wherein said vision priority zone is configured with a predetermined second optical design, said second optical design selected to control a condition selected from the group consisting of: peripheral defocus and other optical aberrations.

12. The optical device according to claim 11, wherein said control of the forward-backward positions of peripheral off-axis focal points by said vision treatment zone further comprises controlling the forward-backward positions of peripheral line foci produced by astigmatism relative to the retina, for a vision treatment device that in combination with the eye exhibits astigmatism.

13. The optical device according to claim 12, wherein said control of the forward-backward positions of peripheral line foci by said vision treatment zone further comprises:

positioning a first peripheral line focus, which is nearer to the cornea of the eye than a second peripheral line focus, to a distance from the cornea of the eye towards the peripheral retina, said distance being approximately less than or equal to the distance from the cornea to the peripheral retina.

14. The optical device according to claim 13, wherein at least one of said vision priority zone is configured to include a region of said optical device, said region selected from the group consisting of: the optical center; the distance visual point; the near visual point; and combinations thereof.

15. The optical device according to claim 13, wherein at least one of said vision priority zone is configured to include the distance visual point and the near visual point on said optical device.

16. The optical device according to claim 12, wherein said control of the forward-backward positions of peripheral line foci by said vision treatment zone further comprises positioning a first peripheral line focus, which is further from the cornea of the eye than a second peripheral line focus, to a distance from the cornea of the eye towards the peripheral retina, said distance being approximately greater than or equal to the distance from the cornea to the peripheral retina.

17. The optical device according to claim 16, wherein at least one of said vision priority zone is configured to include a region of said optical device, said region selected from the group consisting of: the optical center; the distance visual point; the near visual point; and combinations thereof.

18. The optical device according to claim 16 wherein at least one of said vision priority zone is configured to include the distance visual point and the near visual point on said optical device device.

19. The optical device according to claims 14, wherein the minimum width of said vision priority zone is approximately equal to or greater than the size of the entrance pupil of an eye.

20. The optical device according to claim 17, wherein the minimum width of said vision priority zone is approximately equal to or greater than the size of the entrance pupil of an eye.

21. The optical device according to claim 17, wherein said optical design of said vision priority zone that includes the optical center of said optical device comprises an optical design for the control of spherical aberration.

22. A device comprising an optical lens system, said system comprising:

a vision treatment zone and at least one vision priority zone;

wherein said vision treatment zone is configured with a predetermined first optical design, said first optical design selected to effect the control of the forward-backward positions of peripheral line foci of astigmatism, whereby a first peripheral line focus that is nearer to the cornea of an eye than a second peripheral line focus, is positioned to a distance from the cornea of an eye towards the peripheral retina of the eye, said distance being approximately less than or equal to the distance from the cornea to the peripheral retina, while substantially simultaneously controlling a forward-backward position of an on-axis focal point near to the retina; and wherein at least one of said vision priority zone is positioned to include the optical center of said lens system with said vision priority zone that includes the optical center being substantially simultaneously configured with a predetermined second optical design;

said second optical design selected to control at least one condition selected from the group consisting of: defocus, spherical aberration, astigmatism and coma; and wherein the minimum width of said vision priority zone that includes the optical center is approximately greater than or equal to the entrance pupil size of the eye.

* * * * *

UNITED STATES PATENT AND TRADEMARK OFFICE
CERTIFICATE OF CORRECTION

PATENT NO. : 7,665,842 B2  Page 1 of 1
APPLICATION NO. : 11/622246
DATED : February 23, 2010
INVENTOR(S) : Ho et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 430 days.

Signed and Sealed this

Seventh Day of December, 2010

David J. Kappos
*Director of the United States Patent and Trademark Office*